US008821467B1

(12) United States Patent
Minella

(10) Patent No.: US 8,821,467 B1
(45) Date of Patent: Sep. 2, 2014

(54) ABSORBENT ARTICLE WITH FRONT WAIST BELT

(76) Inventor: Lisa Minella, Milwaukee, WI (US)

( * ) Notice: Subject to any disclaimer, the term of this patent is extended or adjusted under 35 U.S.C. 154(b) by 996 days.

(21) Appl. No.: 12/218,569

(22) Filed: Jul. 16, 2008

Related U.S. Application Data

(60) Provisional application No. 60/959,751, filed on Jul. 16, 2007.

(51) Int. Cl.
*A61F 13/15* (2006.01)
*A61F 13/20* (2006.01)
*A61F 13/64* (2006.01)
*A61F 13/49* (2006.01)

(52) U.S. Cl.
CPC ........... *A61F 13/64* (2013.01); *A61F 13/49003* (2013.01); *A61F 13/49004* (2013.01)
USPC ....................................... 604/385.15; 604/392

(58) Field of Classification Search
CPC .................... A61F 13/49003; A61F 13/49004; A61F 13/64
USPC ......... 604/392, 394, 391, 396, 395, 398, 399, 604/400, 401, 402, 358, 386, 397, 385.15, 604/385.23
See application file for complete search history.

(56) References Cited

U.S. PATENT DOCUMENTS

| | | | | |
|---|---|---|---|---|
| 1,224,756 A | * | 5/1917 | Laing | 604/394 |
| 2,058,509 A | | 10/1936 | Rose | |
| 2,516,951 A | | 8/1950 | Brink | |
| 2,577,398 A | * | 12/1951 | Blake | 604/394 |
| 2,863,455 A | * | 12/1958 | Holce | 604/398 |
| 3,050,063 A | * | 8/1962 | Margraf | 604/399 |
| 3,351,062 A | * | 11/1967 | Ferguson | 604/394 |
| 4,051,854 A | * | 10/1977 | Aaron | 604/394 |
| 4,338,938 A | * | 7/1982 | Seavitt | 604/377 |
| 4,773,906 A | * | 9/1988 | Krushel | 604/391 |
| 4,838,886 A | * | 6/1989 | Kent | 604/392 |

(Continued)

OTHER PUBLICATIONS

EcaWare Baby, LLC [online] [retrieved on Feb. 6, 2008] Retrieved from the internet: <URL: http://www.ecawarebaby.com> Website of the inventor herein, Lisa Minella.

*Primary Examiner* — Tan-Uyen T Ho
*Assistant Examiner* — Peter S Vasat

(57) ABSTRACT

A washable absorbent article with a front portion, a back portion and a crotch portion therebetween. The article is constructed with a fully detachable one-piece adjustable belt which is hidden from view when the article is adorned. The belt attaches to rear sideflaps from opposing ends wherein alternate sized belts can be interchanged. Alternative hidden adjustable belts comprise partially detachable one piece units or elongated extensions of the rear sideflaps; and are intended to be wrapped around the waist of the user so the absorbent article can remain in place while a user is performing bodily functions. The belts can be partially or fully detached if a pull up underwear type garment is desired. The front portion is constructed to be brought up between the legs wherein the front portion elongated side flaps are attached to the rear portion of the article to assume a pant like shape. The caregiver may use existing attachment means to keep the absorbent article away from the genitalia while the wearer is performing bodily functions, including fastening front portion sideflaps to back portion sideflaps or laundry securing tabs. Additional washable external absorbent pads can be secured on the absorbent article for added absorbency. Furthermore, the article can be provided with leg coverings by affixing the absorbent body onto open crotch pants.

20 Claims, 18 Drawing Sheets

(56) References Cited

U.S. PATENT DOCUMENTS

| | | |
|---|---|---|
| 5,445,628 A | 8/1995 | Gipson et al. |
| 5,569,229 A | 10/1996 | Rogers |
| 5,899,896 A * | 5/1999 | Suprise et al. ................. 604/391 |
| 6,102,899 A | 8/2000 | Yimin |
| 6,168,585 B1 * | 1/2001 | Cesco-Cancian ........ 604/385.26 |
| 6,605,071 B1 | 8/2003 | Gray et al. |
| 6,616,648 B2 | 9/2003 | Hermansson et al. |
| 6,626,882 B2 | 9/2003 | Hjorth |
| 6,648,871 B2 | 11/2003 | Kusibojoska et al. |
| 6,911,024 B2 | 6/2005 | Kusibojoska et al. |
| 6,955,668 B2 | 10/2005 | Almberg et al. |
| 7,008,410 B2 * | 3/2006 | Gustin et al. ................... 604/392 |
| 2001/0034511 A1 * | 10/2001 | Hermansson et al. ........ 604/386 |
| 2004/0186456 A1 * | 9/2004 | Nawata et al. ................ 604/387 |
| 2004/0236304 A1 * | 11/2004 | Coates et al. ................. 604/393 |
| 2005/0022291 A1 * | 2/2005 | Coates et al. ..................... 2/400 |
| 2005/0027280 A1 | 2/2005 | Patty-Brown et al. |
| 2005/0131382 A1 * | 6/2005 | Brud et al. .................... 604/401 |
| 2005/0210560 A1 * | 9/2005 | Coates .............................. 2/106 |

* cited by examiner

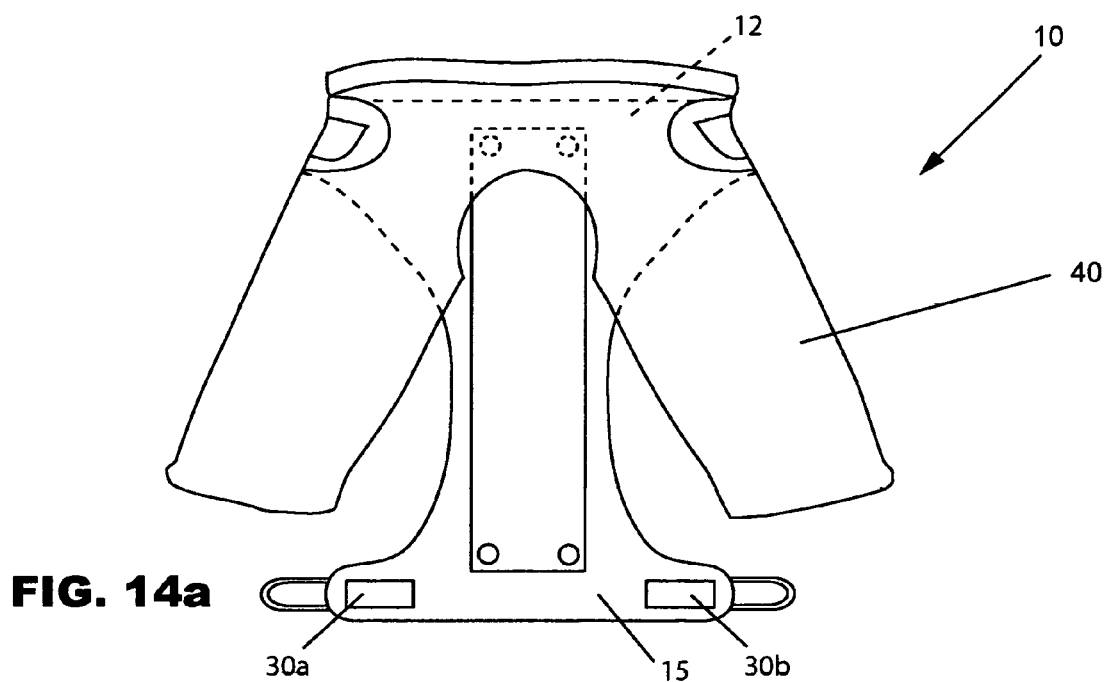
FIG. 14a
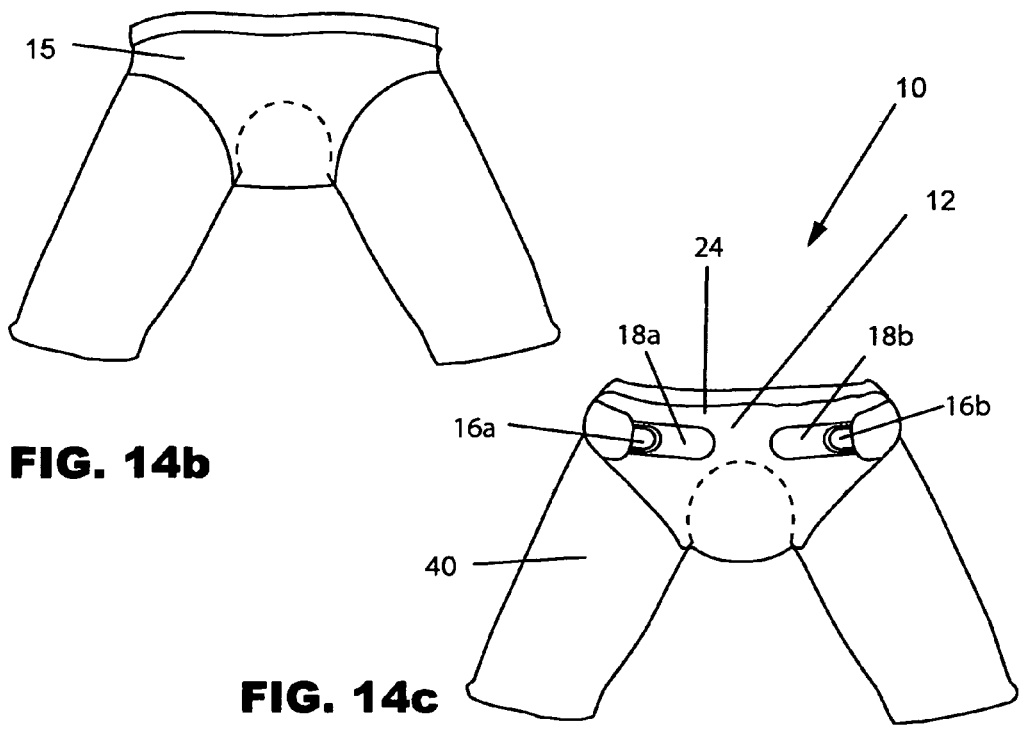
FIG. 14b
FIG. 14c

ABSORBENT ARTICLE WITH FRONT WAIST BELT

CROSS-REFERENCE TO RELATED APPLICATIONS

This application claims the benefit of PPA Ser. No. 60/959,751 filed 2007 Jul. 16 the present inventor, which is incorporated by reference.

FEDERALLY SPONSORED RESEARCH not applicable

SEQUENCE LISTING OR PROGRAM not applicable

BACKGROUND OF INVENTION

1. Field of Invention

The present invention refers to reusable absorbent articles for infants, toddlers, incontinent adults and the like, and more specifically to washable belted configurations for use in potty training or adult toilet usage.

2. Discussion of Prior Art

In the United States today, there is an emerging movement currently practiced in certain natural circles of parenting called Elimination Communication (EC), Natural Infant Hygiene, and/or Infant Potty Training. This practice involves tuning into an infant or toddlers subtle or obvious cues that indicate that he or she has to expel waste as well as learning the time intervals in which their dependent frequently eliminates. Then, instead of leaving no alternative other than excreting in his or her diaper, the caregiver holds the infant over a toilet, potty chair, or other appropriate waste receptacle and allows the baby to perform bodily functions there. In the case of an older baby or toddler, they are then led to the appropriate receptacle and helped appropriately as needed for their current age. This can be practiced starting as early as birth or anytime up to potty training years, which in the US is between 2 and 3 years.

Practitioners believe this type of nurturing facilitates greater understanding between the child and caregiver, keeps the child more comfortable, reduces rash, reduces diaper use, etc. Another important aspect of this method is its perceived gentleness on the environment because of minimal diaper usage.

Though a marginal segment of US society and other western cultures are beginning to practice Elimination Communication, it is quickly gaining momentum due to publicity on major television stations such as NBC, ABC, and FOX news and newspapers such as Washington post, New York Times, etc. Even though this practice is becoming more acceptable and known, many caregivers are still self-conscious about the practice because of its obscurity. The clothing options available, which facilitate ease of frequent bathroom trips, only add to the embarrassment. So many caregivers opt to use traditional baby clothing, despite the inconvenience.

Therefore, many practitioners use traditionally constructed diapers to contain accidents when cues are missed. Though it should be noted there is an overwhelming preference to use cloth diapers rather than disposable, single use diapers. Practitioners' believe disposable diapers hinder potty learning, and have negative environmental, health, and financial impacts. They believe disposable diapers confuse babies as to the outcome of excreting because the inner layer that rests against a baby's skin tends to stay dry after releasing urine. Many people believe disposable diapers may be the reason that the potty training age in the US is at an all time high of 36 to 39 months. Natural Infant Hygiene practitioners pride themselves in being 'natural'. Disposable diapers are not considered natural because of the chemicals used therein, including dioxin, super absorbent polymers, and tributyl-tin. Environmental concerns range from excessive landfill space and long decomposition times, to the amount of raw materials used. Practitioners' also feel that paper and plastic can't be as healthy or comfortable as cloth, and contribute the rise in diaper rash to disposables.

For these reasons as well as the financial burden of purchasing single use diapers when cloth alternatives cost thousands less, the vast majority of people who practice Elimination Communication use cloth diapers, training pants, or other washable types of clothing when they need back up for this method.

One problem EC practitioners find regarding traditional clothing and diapers relates to the frequency in which infants eliminate bodily fluids. Completely disrobing an infant as often as every 20 minutes can be very frustrating for the caregiver and infant alike. Disrobing a squirmy baby or resistant toddler can also be very difficult.

As stated, many people use reusable cloth diapers or reusable cloth training pants as a backup for this practice in case of missed cues. Traditional pants or shorts can make the frequent disrobing process more time consuming and frustrating, so they employ the use of baby legwarmers to cover the legs instead of pants, shorts, or other traditional baby clothing. However, this still causes frustration because putting a conventionally configured diaper back on and off is time consuming and many babies do not like being placed on their back to get a diaper refastened, especially so often.

Some caregivers do employ other types of clothing made especially for Infant Potty Training, despite the drawbacks. One commonly used item is known as "prefold belts," which are elastic waste bands covered in a tube of fabric. These are placed around a babies belly and a flat, unshaped, washable cloth diaper is tucked in the back and front waistband between the baby's legs. The front is then flipped down for fast access to genitalia. One problem with these is their appearance, which mimics that of a loincloth and can therefore be embarrassing. Also, waterproof coverage is sometimes desired, which this method cannot accommodate. Also, the fit is poor and excreta can easily escape. Furthermore, the flat diaper can easily slip out of the belt at unplanned times, leaving undesired consequences such as excrement on the child's legs or the floor.

Yet another type of garment used in this practice are what are known as "split crotch pants" or "open crotch pants". This is the preferred garment in China, where this method of accommodating a child's elimination needs, are the norm. This is a leg covering trouser type pant with an opening in the crotch region, which exposes the genitalia. Although in China it is acceptable for a child's genitalia to be exposed, it is not preferable in this country. Plus, a child excreting waste in populated public areas in China is socially acceptable, but it would be scorned upon in the United States for excrement to be released on the ground wherever a child needed to release it. In addition, it may be undesirable to have exposed genitalia in cold weather.

Many parents prefer their child to go naked to ease the process of Infant Potty Training, but that has obvious limitations as well and cannot always be practiced.

There remains a need for a garment that is easy to use and fits the social climate of our country. There is a great need in these circles also for an environmentally friendly product that can help reduce the mess of accidents, yet can be manipulated quickly and easily to facilitate frequent bathroom trips.

It is also important that the article remains sufficiently away from the genital area while the user is excreting waste. From newborn to toddler age a child is assisted in using the bathroom facilities in a multitude of different positions and holding arrangements. This differs significantly based on receptacle used, age of child, physical ability of child, temperament and preference of caregiver and child. There remains a need for an absorbent article that can accommodate these changing needs.

Also, there remains a need for a product of this type that can contain accidents well.

It is important that the article be of utmost comfort to the user since this is an important aspect of Elimination Communication. Furthermore, there remains a need for an absorbent article that has visual appeal and would not make the caregiver or child feel embarrassed. This article also should be constructed so it can be worn as outer garment of clothing. A garment that has easy access to genitalia and doesn't require articles of clothing on top to be removed would be greatly desired.

Also, since a child's urination amounts can differ greatly with age, time of day, liquid consumed, etc. it is important to have an article which can accommodate these changing needs without the need to purchase separate items.

Another feature of importance is a garment of this type having great adjustability in terms of structure to accommodate infant potty training through toddler potty training.

Prior art does not address all of these important aspects and is not currently in use in this practice for various reasons. U.S. Pat. No. 6,102,899 (Aug. 15, 2000) Yimin shows a disposable training pant with a detachable flap. This flap is positioned only for the release of feces in a toilet. This would not suffice in the case of a caregiver practicing EC.

So-called belted diapers could aid in this process, but there are significant disadvantages to the prior art if used in these circumstances. Although the prior art solves many problems associated with belted absorbent garments, they do not address important issues related to Elimination Communication practitioners' needs.

For one, most prior art belted diapers are disposable, single use items. Besides the environmental and health concerns related to these single-use absorbent articles, there is a significant problem with comfort. Most prior art belted diapers have belts that extend from the back wings and join around the waist of the user with a securing means such as VELCRO™. When VELCRO™ or other hook and loop type fasteners are secured on a relatively thin belt around the waist of a user, it causes discomfort and irritation. Worse yet, it can cause chaffing, skin injuries or even infection since it is an area of close contact with excreta. Because of the typical fat accumulation on babies stomach regions, it is virtually impossible to keep the hook and loop out of contact with the abdomen. When a baby with an adipose stomach region is sitting down, their fleshy abdomen rests on the top horizontal belted waist portion of the diaper and can likely get scraped by the edges of the plastic or paper diaper and the top and bottom portions of the hook and loop. Even if the diaper is constructed so that the joining mechanism is inward from the longitudinal edges, the sitting child's front waist region can bend and deform the belt from its intended structural position, exposing the rough edges. These problems would be even more pronounced in the desired washable garment because the washable hook and loop fasteners on the market have even rougher, sharper edges than the paper or plastic hook and loop type fasteners.

An added area of discomfort stemming from disposable prior art belted garments is the area of frontal attachment concerning the front of the diaper to the belt portion, which when engaged assumes the diaper a pant like shape. Belted diapers have a back portion, a front portion, and an intermediate crotch portion. Once the belt is secured, the front portion suspended between the legs is generally raised up between the legs and attached onto the belt. This further aggravates the frontal abdomen region and can cause possible problems due to skin irritation. Once again, in a washable configuration the hook and loop would be of even greater concern because of the sharper edges.

This also leads to another problem with prior art regarding the front portion attachment location. When a diaper, training pant or other absorbent article is releasably secured on the waist belt, it is difficult to attach in a way that the front panel lays smoothly in its intended position. It is common to have to attach and reattach several times before the garment lays flat and uniform with both sides parallel as intended. This may be easily accomplished on an older user, but on a squirming baby or toddler, or on a baby with abundant abdomen flesh it is very difficult.

In addition, this securing location often lends to the hips of the wearer exposed, giving the article an undesirable loincloth type appearance.

Another problem common with belted absorbent garments pertains to when the belt is set on its smallest settings; adjusted for a child with a small waist. The remaining free ends of the belt suspend down the front of the waist region and possibly down further causing irritation to the genitalia.

Finally, belted disposable diapers are expensive to manufacture. The belt area is of particular concern because the expense it adds to the manufacturing process.

U.S. Pat. No. 6,955,668 Almberg (October 2005), U.S. Pat. No. 6,911,024 Kusibojoska (June 2005), U.S. Pat. No. 6,648,871 Kusibojoska (November 2003), U.S. Pat. No. 6,626,882 B2 Hjorth (September 2003), and U.S. Pat. No. 6,616,648 Hermansson (September 2003) all teach embodiments of disposable absorbent articles which include two belt portions that join together at the waist, and where the front portion that is raised between the legs secures on the belt.

U.S. Pat. No. 5,445,628 Gibson et al. (August 1995) shows a belted garment in which the belt is a separate unit from the chassis; yet they are constructed to releasably attach. In this case the belt is washable, which would lend to more comfort for the user. Yet, the problem remains with a disposable chassis and the front panel securing to the belt.

In the crowded art of absorbent articles, limited prior art exists which teaches reusable, washable belted absorbent garments. U.S. Pat. No. 2,516,951 M. E. Brink (April 1947) teaches a reusable belted diaper. This invention suffers because the front panel that is brought up between the legs is secured with snaps on the front body of the diaper below the waistband. This would be a difficult area to secure on an energetic baby. Also, securing in this area could easily lend to leaking excreta, and a compromised fit.

U.S. Pat. No. 2,058,509, D. Rose (January 1936) also teaches a washable absorbent diaper with a waistband. This invention does lend to the comfort of a baby by being devoid of all mechanical fasteners, instead relying on waistband elastic. The invention suffers from an endless band, instead of a belt type configuration that can be released. When the user has a bowel movement, sliding a diaper with an endless band down his or her legs can spread excrement on the users body. This type of arrangement is also more difficult to adorn and remove. The front portion of the article, which is pulled up between the dependents legs, is also attached to the front waistband. While comfort would probably not be an issue with this particular diaper, exemplary fit, leakage control, and ease of attachment would be.

U.S. Pat. No. 6,605,071 Gray, et al. (Aug. 12, 2003) shows a washable absorbent garment provided with a release panel that connects on the front of a wearer's body, below the waistband. The main purpose entails allowing a caregiver to have expedient access to change a disposable liner without removing the garment. This article suffers from an endless waistband. Other problems pertain to the area of frontal attachment, which may tend to leak, cause discomfort, and be difficult to attach on a baby.

None of the prior art teaches an adequate method which aids in keeping the hook and loop or mechanical attachment means undoubtedly away from the sensitive skin of the baby when the baby is held in "classic position" for Elimination Communication. In "classic position" the caregiver holds the baby's legs under the thighs, while the babies back is resting against the caregivers torso, and the child is positioned away from the caregiver with his or her genitalia over an appropriate waste catching receptacle. In Patent Application Publication 2005/0027280 Patty Brown et al. (February 2005) teaches a disposable absorbent article in which the front panel can be attached to the center rear waist belt when a toddler is sitting on a toilet. While this can work properly for a toddler, it cannot sufficiently accommodate the needs of a caregiver with an infant in classic position.

There also remains a need for an absorbent article which takes into account the different ages, stages, and phases an infant to a toddler goes through regarding potty training. For example, a child reaches an age when they try to take a diaper off at undesirable times. There also comes an age when it is desirable for the child to remove the absorbent article by themselves to aid in potty independence. There is a need for a training pant that makes it difficult for a baby to take off a diaper at the same time having the adjustability to make it possible when desired.

Also, it would be of great value to have an article that can keep a baby comfortable in all types of weather without covering the releasably attachable front panel. An absorbent article which can easily be attached to split crotch shorts or pants without changing sizes or dimensions of the absorbent article would be greatly desired.

It is also of great importance to have an article which is easy to care for. An article that can be washed and dried in a regular washing and drying cycle is of utmost importance. Also, the hook portion of washable hook and loop can easily gather hair and other debris which is very difficult to remove and also compromises the securing ability of the closure. It is important to provide a novel way to use hook and loop without this problem. Finally, typical washable diapers with hook and loop have the added problem of having the hook secure to other clothing in the laundry, thus damaging delicate items and making it difficult to separate clothing items after washing and drying.

SUMMARY

The present invention attempts to solve the aforementioned problems. The absorbent article is comprised of washable, reusable materials. It is comprised of a front portion, a rear portion and an absorbing crotch portion there between. The absorbent article is further supplied with a belt which extends from rear portion side flaps and which is intended to be wrapped around the waist of the user, thereby allowing the article to remain on the user while they are performing bodily functions. The belt is not visible when the absorbent article is fully secured on a user, thereby providing a diaper that appears as a type of normally constructed diaper and does not induce embarrassment to the user or caregiver. The hidden belt can be comprised of a one piece unit that has fasteners on opposing lateral ends which connect to the rear portion side flaps of the absorbent article, thereby the belt is detachable and can be interchanged with belts of various sizes. The hidden belt can also be an adjustable one piece unit that permanently secures to one rear portion and releasably attaches to the opposing rear portion. Another possibility is an adjustable hidden belt which is elongated extensions of the rear side flaps and is secured with snap fasteners. The belts are further characterized in that they do not secure with hook and loop at the waist, thus keeping the abdomen sufficiently away from sharp edges. The belts can be fully or partially detached in a manner that transforms the absorbent article into a pull up underwear type garment, which is desirable for independence seeking children. The front portion is constructed to be brought up between the legs wherein the front portion side flaps can be connected to the rear portion, whereby the attachment point is dependent on the waist size of the wearer. As such, a belted absorbent article of this type lends to a greater sizing range, harder to disengage tabs for younger children, ease of application and intended position of front portion, and safety and comfort with attachment means located away from the stomach region. Additionally, the absorbent article benefits from the location of the rear portion receiving fasteners as they can also be utilized in keeping the absorbent article away from the genitalia when the front portion is brought back through the legs and is attached to the existing rear side flaps or back portion when excretion is performed. Existing loop receiving laundry securing tabs can also be utilized to keep hook away from wearer when the training pant is in a suspended position. Furthermore the article can be supplied with external absorbent pads for additional absorbing capabilities which can be secured by pocket means or other fasteners such as snap fasteners, retaining bands, hook and loop, or equivalents. In this manner, additional garments with higher absorption capabilities will not need to be purchased, and drying time will remain minimal. The article is also constructed with a quick drying sewing method of the internal absorbent pad for ease of care. Hook tabs supplied with binding also provides ease of care in that hair and other debris does not adhere to them aggressively in this manner, and also supplies additional safety to the skin. Furthermore, the rear portion of the absorbent article can be permanently secured to open crotch or split crotch pants, whereby the genitalia can still be quickly accessed without the hindrance of clothing on top of the absorbent article. Further features are evident in the following description.

DRAWINGS

FIG. 1 illustrates a partially assembled diaper according to the first embodiment of the invention FIG. 2a is a perspective sideview of the absorbent article in a partially attached position FIG. 2b is a sideview of the absorbent article in a fully attached position FIG. 3a, b are front views highlighting the absorbent soaker pad.

FIG. 4a, b, c, d are back views of the absorbent article of various embodiments

FIG. 5a, b, c are front views of a preferred embodiment of the adjustable attachment waist component, or belt FIG. 6a is a front view of an embodiment of a belt FIG. 6 *b, c,* are side views of the embodiment of the belt illustrated in 6*a*

FIG. 6*d* is a front view of the belt showed in 6*a* set on the smallest setting FIGS. 6*e* and 6*f* is a front view of the belt, pre-secured in 6*e* and then secured in 6*f* to the topsheet to prepare for use in pull up underwear like configuration FIG. 7 shows another alternative embodiment of the belt from a front view FIG. 8*a, b* shows perspective view of the absorbent article in a rear attachment position for use when assisting a child with excreting in a receptacle FIG. 8*c, d* shows back views of the absorbent article in rear attachment position for use when assisting a child with excreting in a receptacle FIG. 9 *a*, 9*b* shows front view of a partial topsheet focusing on the hook fasteners FIG. 10*a, b,* and *c* show front views of the topsheet with pockets added FIG. 11 shows a front view of the topsheet with an external soaker added FIG. 12*a, b* shows front views of the topsheet with retaining bands for an external soaker pad FIG. 13 shows a front view of the training pant with an external pad FIG. 14*a* shows a front view of an absorbent article affixed to open crotch pants with the front portion an open state FIG. 14*b* shows a front view of the absorbent article affixed to open crotch pants in a fully secured, wearable state FIG. 14*c* shows a back view of the absorbent article affixed to open crotch pants in a fully secured, wearable state FIG. 15 shows a front view of the article in a secured state

DETAILED DESCRIPTION

The term 'absorbent article', 'diaper', 'training pant', 'absorbent garment' and combinations thereof are used interchangeably in the following detailed description to refer to the present invention or to refer to any article worn on a body to absorb, retain and isolate bodily wastes.

The terms 'releasably attach(ed)' 'releasably secures' 'detachable' 'refastening means' 'resecures' and 'refastenable' refers to a portion of the article which can be attached, detached and attached again more than once without compromising the structure or adhesiveness, and without damaging the article in any way.

The term 'accident' or 'miss' refers to a situation when a diaper user excretes bodily fluid in an absorbent article or anywhere other than an intended human waste receptacle.

The term 'sewn' is used herein to refer to an attachment method that uses needles and thread. It can be used to indicate serging, coverstitching, manual sewing, or any other method of binding together fabric and other sewing materials. If another term is used instead of 'sewn' the alternate term is the preferred method.

The term 'go to the bathroom' refers to the situation when a person uses a toilet or other receptacle to release bodily wastes into.

FIG. 1 shows an embodiment of a reusable absorbent article 10 comprising a topsheet 26, a backsheet 24, and an absorbent pad 28 sandwiched therebetween. The article has a longitudinal direction represented by dashed line 50 that runs parallel to the absorbent core pad 28 and a latitudinal direction represented by dashed line 51 that runs perpendicular to the absorbent core pad 28. It is further constructed with a front portion 15, a rear portion 12, and an intermediate crotch portion 13. The article is contoured in a body mimicking shape, whereas the rear portion 12 is provided with a construction that is widest on the latitudinal waistline and tapers considerably to the crotch region 13. The front portion 15 is widest at the waistline and also tapers to the crotch portion 13. The rear portion 12 is constructed with latitudinally extended or elongated side flaps 11*a*, 11*b*. The front portion is 15 also constructed with latitudinally extended or elongated side flaps 14*a*, 14*b*. The article is further provided with an adjustable waist attachment component, or belt 20, which can be releasably attached to the rear side flaps 11*a*, 11*b*. Hook material 16*a*, 16*b* which releasably attaches to loop material 18*a*, 18*b* is connected to the front portion side flaps 14*a*, 14*b*. The hook fasteners 16*a*, 16*b* are encased in a binding material 17*a*, 17*b*. The loop material fastener 18*a*, 18*b* is sewn on the rear portion 12 generally starting at a predetermined point from the terminal endpoint of the rear side flaps 11*a*, 11*b* and ending at a predetermined point toward the mid rear region, creating two symmetrical fastener pieces adjacent one another in this embodiment. Laundry tabs 30*a*, 30*b* for securing the hook when washing or when assisting a baby using waste facilities are sewn relatively adjacent to the hook tabs 16*a*, 16*b*. Elastic 22*a*, 22*b*, 22*c* is encased in this embodiment between the topsheet 26 and backsheet 24. Leg elastic 22*a* is sewn from the rear portion 12 to the front portion 15 starting at predetermined points near the front 14*a*, 14*b* and rear 11*a*, 11*b* side flaps. Rear elastic 22*b* is encased at the top waistline and sewn transversely at a predetermined length. Front elastic 22*c* is hidden between the topsheet 26 and backsheet 24 and is sewn at a predetermined length across the top waistline.

The topsheet 26 can be comprised of any soft liquid permeable material. A woven or nonwoven material that allows the user to feel wetness against the skin such as various cottons and cotton blends, eco-friendly or organic fabrics such as bamboo, hemp, etc. would be desirable. These fabrics include bamboo velour, cotton velour and combinations thereof, birdseye, terry cloth, stretch terry, French terry, sherpa, flannel, interlock knits, diaper twill, hemp fleece, cotton fleece, bamboo fleece, diaper gauze, etc. A topsheet 26 material that wicks moisture away from the body would also be desirable in times where it is not desirable to feel exudates against the skin, such as when a user is attempting to sleep, restricted in a car seat, etc. Washable fabrics which pull moisture away from the skin and direct the liquid into the absorbent pad 28 include, but are not limited to, polyester based fleece, microfleece, polyester velour, suedecloth, and the like.

The backsheet 24 can be a waterproof material such as a woven or nonwoven fabric laminated with polyurethane laminate (PUL) which is available at Fabrite Laminating Corporation in Woodridge, N.J. Other water impervious materials appropriate for the backsheet 24 include fleece, wool, and other types of laminated fabric, for instance. The backsheet 24 can also be fluid pervious for the purpose of feeling more similar to real underwear or for greater breathability.

The topsheet 26 and backsheet 24 are joined together by sewing with polyester thread. Polyester thread keeps the urine from wicking to the backsheet 24 of the diaper, as is important with the waterproof version. In this embodiment they are sewn together using the turn and topstitch method, which is well known in the art. A seam allowance is left intact for the purpose of sewing the elastic onto. The topsheet 26 and backsheet 24 can also be joined together by method of serging which is also well known in the art. Another method of joining the topsheet 26 and backsheet 24 is by employing the use of fold over elastic or other elastic and binding methods. Fold over elastic, which is elastic binding with a seam down the center for the purpose of easily folding it in half while sewing, is also well known in the art.

FIG. 2a is a perspective sideview of the absorbent article in a partially attached position FIG. 2b is a sideview of the absorbent article in a fully attached position FIG. 3a shows a front view of the sewing method of the absorbent pad 28. The absorbent pad 28 can be composed of any material which can absorb liquid. Common materials in use include textiles with a primarily cotton content, such as sherpa, fleece, birdseye or various forms of terry cloth. Also used are various types of bamboo, hemp or microfiber. These and other absorbent fabrics are suitable. Generally the absorbent pad 28 is composed of two or three layers of material which are sewn or serged together. The absorbent pad 28 has a width approximately 3 inches and the length varies depending on the size of the topsheet 26 and backsheet 24. Generally it is the length of the topsheet 26 and backsheet 24 minus a few inches. It is centered onto the topsheet 26. It is sewn to the topsheet 24 where it will be hidden between the topsheet 26 and backsheet 24 and in turn will be considered an internal absorbent soaker pad 28. The pad is sewn in a novel way to promote quicker drying time after washing. The pad 28 as shown in FIG. 3a is sewn at the top horizontal edge 29a and the bottom horizontal edge 29b of the topsheet 26. It is also sewn only along a portion of the vertical edges. The absorbent pad 28 is sewn along the left vertical edge 29c starting approximately 3 inches from the top horizontal edge 29a and ending about 2 inches from the bottom horizontal edge 29b. The right vertical edge 29d is sewn in the same manner. This way air can circulate while drying; thereby promoting a drying time no more than any other garment in the load. If the absorbent pad 28 is sewn in a continuous square following the shape of the pad 28, drying time is considerably longer; commonly two to three times as long.

FIG. 3b shows an alternative practical method of sewing the absorbent pad 28. FIG. 3b shows the absorbent pad 28 sewn only along the left vertical edge 29c and the right vertical edge 29d of the topsheet 29. The top and bottom edge of the soaker pad 28 are not secured to the topsheet 26. This also promotes quick drying time.

FIG. 4a is a schematic back view of one embodiment of the absorbent article in a fastened state. The loop fasteners 18a, 18b can be APLIX™, which is a sew-on washable material that is well known in the art. The loop fasteners 18a, 18b can also be made with TOUCHTAPE which is well known. The loop fasteners 18a, 18b can also be made with loop fabric, which is softer at the edges. The hook 16a, 16b, and loop fasteners 18a, 18b can be made of any type of this style of fastener, and is not limited to the brands mentioned herein. The hook fasteners 16a, 16b are attached to the elongated front side flaps 14a, 14b and can be attached to the receiving loop fastener 18a, 18b by being brought up between the legs of a user and attached to form a pant like shape. Depending on the waist size of the user, the hook fasteners 16a, 16b secure at the hips or rear of the wearer. FIG. 4a shows the hook fasteners 16a, 16b securing the rear portion 12 of the wearer as would be the case with a person with a smaller waist.

FIG. 4b shows another embodiment of the absorbent article 10 with continuous loop fastener material 18c as a significant top portion of the backsheet 24. This softer, flexible loop fastener material 18c is more like a textile fabric than other hook and loop fasteners. This embodiment provides the hook fasteners 16a, 16b with more receiving material to releasably adhere to, thus expanding the size range for the customer.

FIG. 4c shows another embodiment of the absorbent article 10. In this embodiment the upper region rear portion 12 is supplied with snap fasteners 32a. The front side flaps 14a, 14b are also supplied with snap fasteners 32b. Of course the rear portion 12 and front side flaps 14a, 14b must be supplied with opposite style snap fasteners so they can be engaged. Preferably the rear portion 12 is supplied with sockets, or female snap fasteners and the front side flaps 14a, 14b are supplied with studs, or male snap fasteners. Alternately, the rear portion 12 can be supplied with male snap fasteners and the front side flaps 14a, 14b can be supplied with female snap fasteners.

FIG. 4d shows the absorbent article 10 with s hooks as the fastening means 33a. They are latched with s hook receivers 33b which are made with fabric.

Other mechanical fastening materials may be also be employed. The embodiments are not limited to the aforesaid fastening elements. Other conceivable engaging materials include snap tape, hook and eye, and strong magnetic fasteners.

FIGS. 5a and 5b show a front view of an exemplary embodiment of the adjustable attachment waist component, or belt 20. FIGS. 5a and 5b display a detachable belt. In FIG. 5a the belt is completely detached. The belt 20 is constructed with a soft knit or woven material. It can be the same material that is used for the topsheet 26 as taught in the description in FIG. 1. The belt 20 can be constructed similar to a tube, with the transverse edges turned to the inside. Inside the tube can be a soft elastic which aids in further adjustability of the belt 20. This embodiment of the belt 20 is a continuous tube, which is sewn shut on the lateral ends. Proximal to the lateral ends, snap fasteners are permanently affixed 32a. It can be desirable to place two snaps near one lateral edge of the belt 32a and one snap fastener 32a near the distal edge. Two snaps on one side keep the belt from twisting when trying to secure the opposite end around a dependent's waist. The snaps are made from a strong plastic that is resilient to laundry care on the hottest settings. Polyacetal resin snaps may be used which are available at The Snap Store located in Lawrence, Kans. Belts 20 of various sizes, as shown, can be purchased to adjust the sizing to an even greater degree. A number of at least one receiving snap(s) is permanently attached to both rear side flaps 11a, 11b. They begin at a predetermined distance close to the lateral edges of the rear side flaps 11a, 11b. FIG. 5b shows the belt 20 attached to the rear side flaps 11a, 11b. Of course the belt 20 can be releasably attached from either side flap 11a, 11b easily.

FIG. 5c shows an elastisized belt which is permanently affixed to the left rear side flap 11a and releasably attaches with a snap fastener 32a on the right rear side flap 11b. FIG. 5a, b, c, and d all display the embodiment of snap fasteners 32a as the attachment means on the rear portion 12, rather than hook and loop which was displayed as the attachment means in the previous illustrations.

FIG. 6-7 are alternative belt embodiments which will be described in a following section.

All the belt embodiments described herein FIG. 5-7 are characterized in that they are adjustable, have only attachment means that do not irritate the wearer, and can removed or detached to create a pull on type underwear absorbent garment. Lastly, they all are hidden, which more specifically indicates that when the article is fully secured in its intended position around the waist of a wearer, the belt is not visible; thereby creating a belted diaper that appears as a more standard type diaper which is beneficial to caregivers who want to practice Elimination Communication in a more discreet, yet easy fashion.

FIG. 8a shows a perspective view of the absorbent article 10 attached in one potty ready position on a body 44. The absorbent article is brought back between the legs of the wearer and the hook fastener 16b is folded and attached to the loop fastener 18b on the rear side flaps 11a, 11b. This method is frequently used in classic position.

FIG. 8b shows a perspective view of the absorbent article in another potty ready position on a body 44. Here the article is suspended between the legs and the hook fasteners 16a, 16b are secured to the laundry securing tabs 30a, 30b to keep them away from the skin. This is a preferred method if a wearer is sitting on an infant potty chair.

FIG. 8c shows a back view of the absorbent article placed on the wearer 44 in a rear attachment position. This is a quick way to secure the article when the child is of walking age and wants to get onto an infant potty chair by his or herself. The hook fasteners 16a, 16b are secured to the loop fasteners 18a, 18b in the rear portion 12 so that the child cannot disassemble the training pant. Yet the hook fasteners 16a, 16b remain safely away from the skin due to the position and the hook binding 17a, 17b.

FIG. 8d is identical to FIG. 8c with the exception that the fastening means is snap fasteners 32a.

Operation of Aforesaid Embodiment

It would be beneficial to describe the operation of the aforesaid embodiment and its variations presently. Further embodiments and operations will be discussed subsequently.

This absorbent garment FIG. 1 can be applied to a person while the body is in a multitude of positions. The belt 20 is the first portion to be attached to a wearer. This completely detachable belt FIG. 5a, 5b, is secured on one of the rear side flaps 11a, 11b before it is adorned on the dependent for ease of application. The rear portion 12 of the training pant 10 is placed to cover the rear end of the wearer at the back waistline. The belt 20 is then wrapped around the abdominal region and secured. This can easily be accomplished while a child is lying down on his or her back, while the child is standing, in crawling position, or even sitting. Additionally, if the baby is lying on his or her stomach the belt can also be secured since the attachment means is near either hip. Referring back to FIG. 1, the front portion 15 is then drawn up between the users legs and secured with the extended hook fasteners 16a, 16b or snap fasteners 32a, (depending on the embodiment) to the rear side flaps 11a, 11b. If the user has a smaller waist, the receiving loop area or receiving snap area can be placed all the way to the back rear portion 12, which is evident in FIGS. 4a, 4b, and 4c. The absorbent article then assumes a pant like shape as is evident is FIG. 2b. When it is noticed the dependent then has to use a waste receptacle to release bodily fluids, the front portion 15 of the garment is then released from the backsheet 24 and pulled back between the users legs so it is not covering the genitalia. It can then be releasably attached to the rear sideflap 11a, 11b loop fasteners 18a, 18b or other rear fasteners. This is accomplished by folding the hook fasteners 16a, 16b to the backsheet 24 of the front panel 15, opposite the laundry tabs 30a, 30b, the then simply raising the front portion 15 to secure the hook fasteners 16a, 16b to the loop fasteners 18a, 18b on the rear side flaps 11a, 11b as in FIG. 8b. This description also holds true if using the snap fasteners 32a. Though in this case the snap fasteners 32a on the front side flaps 14a, 14b can be easily secured to any receiving snap fasteners 32a on the backsheet 24. The hook fasteners 16a, 16b can also be secured to the laundry securing tabs 30a, 30b and the article can be left to hang away from the genital area without worry of the hook coming in contact with the babies skin. This would be sufficient for instance when the baby was held in position on an infant potty chair.

Most prior art belted garments of this type secure on the belt at the front waistline. This unique side or rear securing attachment area on a washable belted garment provides the wearer with a garment that looks like a traditional cloth diaper, which is beneficial to the user and caregiver. People who practice elimination communication can then forego the embarrassment and/or difficulty of the clothing options available up until now. The options available until present forced a caregiver to choose between an embarrassing look, or extreme difficulty in continually changing an infant if they adorned traditional clothing.

This absorbent article also provides superior leakage control and fit by securing on the rear portion 12. By the front portion 15 securing to the back portion 12, there is less room for any leakage of exudates to occur, especially since there is significant surface area for the front side flaps 14a, 14b to adhere to. The more adjustability inherent in a diaper, the better the fit will be. The better the fit in an absorbent garment, the less chance of bodily discharges escaping.

The elongated front side flaps 14a, 14b FIG. 1a also aid in a desirable fit. By pulling the front side flaps 14a, 14b into secured position on the backsheet 24, a formfitting, symmetrical shape is born. It is easy to achieve proper alignment with the front portion 15 lying flat in its intended position even with a squirmy or uncooperative child. It also is not difficult to achieve closure with a dependent in a multitude of different body positions. The elastic on the front portion 15 waistband also helps with adjustability, keeping exudates in especially while a child is lying on his or her stomach, and keeping the absorbent garment as form fitting as possible.

The unique belt FIG. 5a, 5b, also aids in additional adjustability. Since the belt 20 can be completely detached, it is easy to replace it with different size belts. This aids in the diaper fitting many size users for periods of time longer than the average diaper. Also, since the belt 20 is made with the same material as the topsheet 26 generally, it is not expensive to manufacture. Therefore, it is not financially prohibitive to create and to purchase additional belt pieces. Once the belt 20 is attached, one will notice that there are no suspended end pieces of the belt that can dangle downward and irritate the user or interfere with the securing mechanism of the front portion 15 to the rear portion 12.

Additionally, the training pant can be secured on the user 44 with the belt 20 removed. Since the front portion 15 secures to the rear portion 12 it is evident from FIG. 2b that the belt is not necessary to keep the diaper secured on a body. Its function is to allow the diaper to be flipped down to use the bathroom. At times when a flip down style training pant is not needed, it may be beneficial to use the training pant with the belt removed. When a child reaches an age where they want to use bathroom facilities more independently, they often resist the help of a caregiver. Removing the belt then effectively turns a belted style diaper into a cloth pull up style; similar to regular underwear. This helps a child feel more 'grown up' and encourages potty learning. The absorbent garment is still supplied with hook and loop, snaps or other closure mechanisms at the sides of course, so removal in case of an accident is easy and relatively clean. Instead of pulling the soiled diaper down over the legs and possibly spreading fecal matter, the sides can easily be unattached allowing the training pant to be removed. To use the training pant in this manner, two methods of applying the absorbent article are recommended. In the first method, the training pant can be applied in the aforementioned manner; first securing the belt 20 around the waist and then raising the front portion 15 to secure to the front side flaps 14a, 14b to the rear portion 12 backsheet 24; albeit loosely. Next, remove the belt 20 from the article 10 and tighten the front side flaps 14a, 14b to the backsheet 24. This is helpful if applying the article in a belted fashion is desirable at the given time. Another method to apply the absorbent garment 10 is simply by removing the belt prior to adorning the body. Secure the front portion 15 to the rear portion 12 and pull over the child's legs. Once the training pant is in place without the belt, it can be pulled on and off like regular underwear with or without the aid of a caregiver.

Descriptions of Additional Belt Embodiments

FIG. 6a is a front view of an embodiment of the waist belt 20 secured on the rear side flaps 11a, 11b. The belt can be constructed with the same materials as the belt described in FIG. 5a; soft textile with encased elastic. In this embodiment the belt 20 is permanently affixed on the left rear side flap 11a. The right distal edge of the belt 20 can be releasably secured to the right rear side flap 11b. This unique belt 20 is constructed with additional snaps 32a on the right portion to facilitate great adjustability without the use of separate belts. It is important that this belt, which is permanently secured on one lateral edge, can still serve very similar functions to the detachable belt described previously. Namely, the belt needs to be adjustable to the point that the training pant can be pulled up and down similar to regular underwear. It also cannot have the disadvantage of end portions which dangle down and can irritate the wearer or interfere with securing the front portion 15 to the rear portion 12 if used on a small waisted body.

Figure 6A:
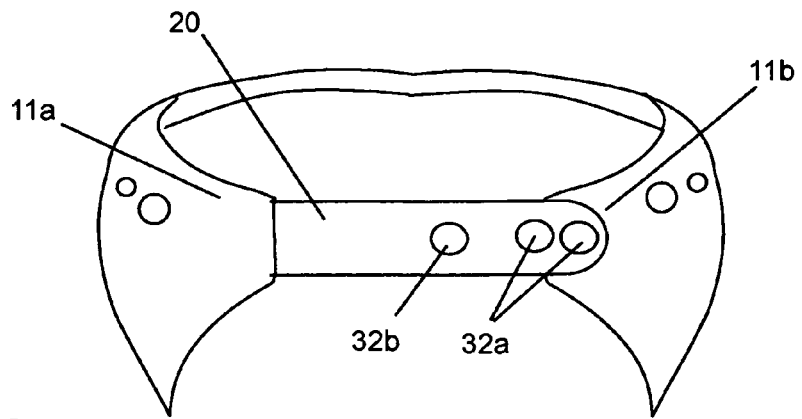
FIG. 6b shows the belt 20 fully stretched from a side view perspective. In this state the belt 20 could be secured to a user; this would be considered the largest setting.
FIG. 6c shows the same belt 20 from a side perspective in the process of being secured.
FIG. 6d shows the identical belt 20 secured on the rear side flaps 11a, 11b with the belt adjusted on its smallest setting.
Figure 6B:
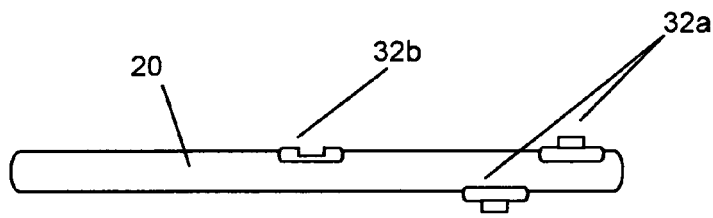
Figure 6C:
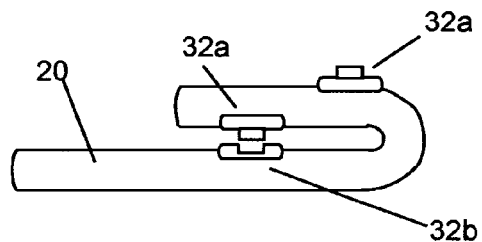
Figure 6D:
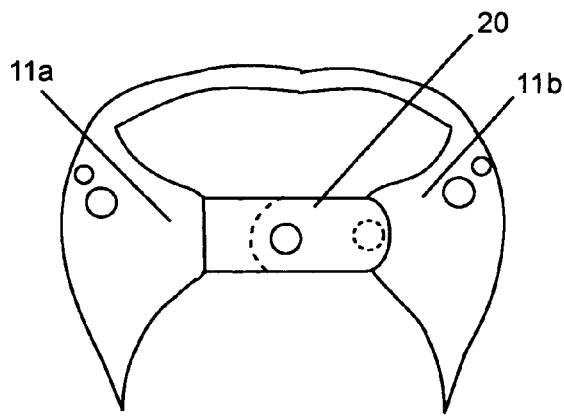
Figure 6E:
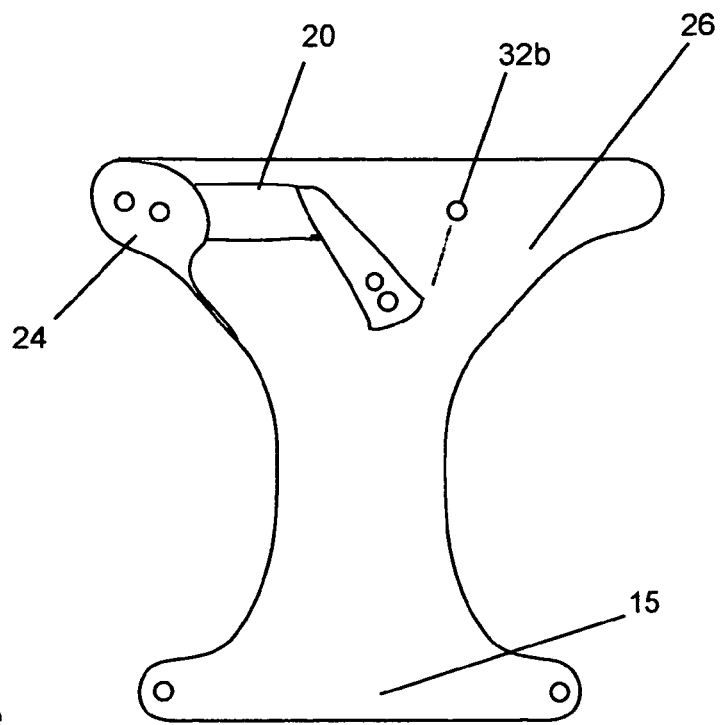

FIG. 6e shows the same belt 20 ready to attach to the topsheet 26. It can be attached to the topsheet 26 by attachment to snap 32a and then rest along the users back waist. In this manner the belt 20 is removed from the function of the training pants, and the training pants can then be secured. The front portion 15 is secured to the backsheet 24 and then the training pant assumes a pant like shape. The training pant is then ready to pulled on and off in the style of traditional underwear.

Figure 6F:
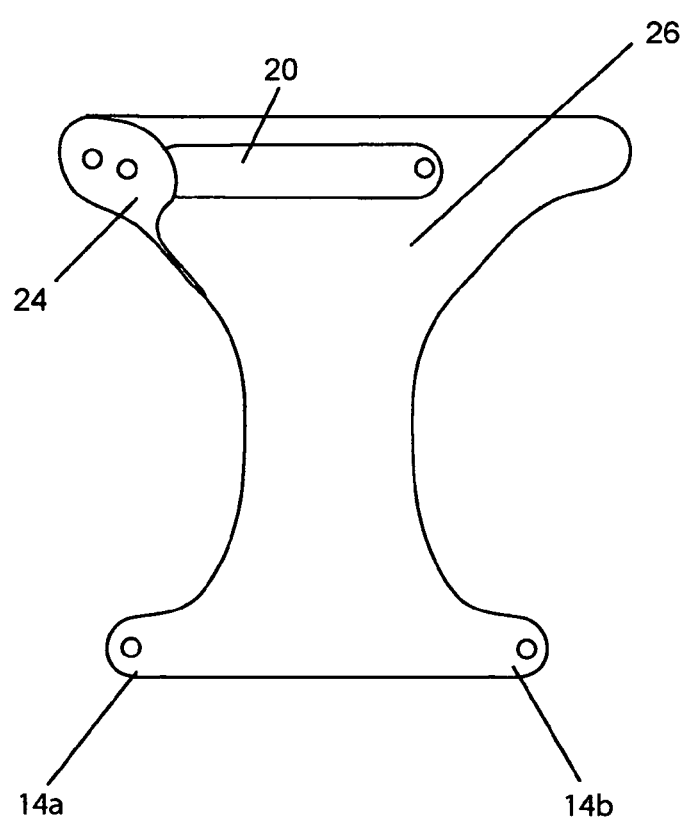

FIG. 6f shows the same belt 20 secured to the topsheet 26.

Operation of Aforesaid Belt Embodiment

The belt 20 as described in FIG. 6a, b, c, d, e, f is secured on a user in an almost identical manner to the previously described belt. The belt has the additional settings, however, for more adjustability. To secure the belt to the rear sideflap 11b on the largest setting as shown in FIG. 6a, simply make sure the belt is unsnapped and fully extended and attach the snap nearest to the lateral end portion to the rear side flap 11b. For a smaller setting, simply shorten the belt as instructed in illustrations 6b and 6c. Then attach to the rear side flap 11b. In FIG. 6d you will notice there are no dangling belt end pieces.

This belt has two forms of adjustability, which consist of encased elastic and additional snaps. With this construction the belt can be made purposefully longer to accommodate for the times when regular style pull up underwear is desired. With the belt on the largest setting which is designed to fit slightly loose around a wearers waist, yet firm enough to hold it in place for pottying needs, the training pant can be pulled up and down by the child. Additionally, an extra snap 32b can be added to the rear topsheet of the 26 of the training pant as in FIG. 6e, 6f to adhere the belt 20 to when it is not desired to be implemented. Simply snap the belt to its smallest setting and attach to the topsheet 26 receiving snap fastener 32b. Thus, the belt 20 is attached in a horizontal position to the upper topsheet 26. Simply fasten the front side flaps 14a, 14b to the backsheet 24 and the article has a functional pant like shape. Pull the garment up and down as you would with regular underwear.

Description of Additional Belt Embodiment

Figure 7:
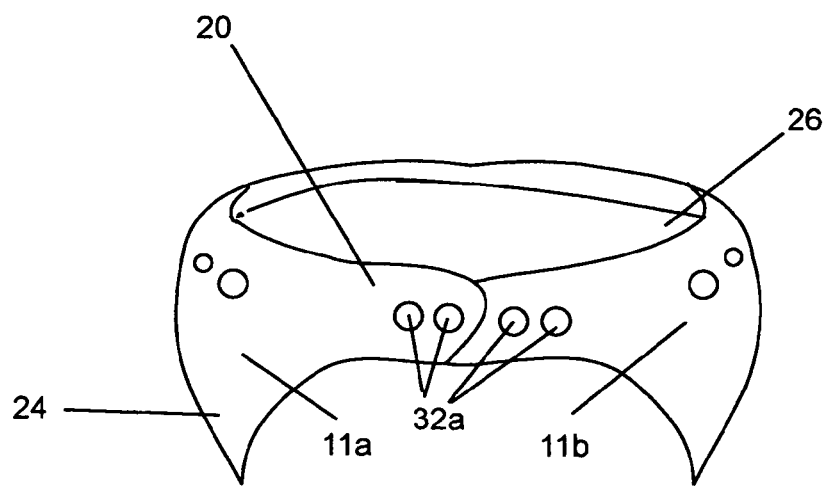
Figure 8A:
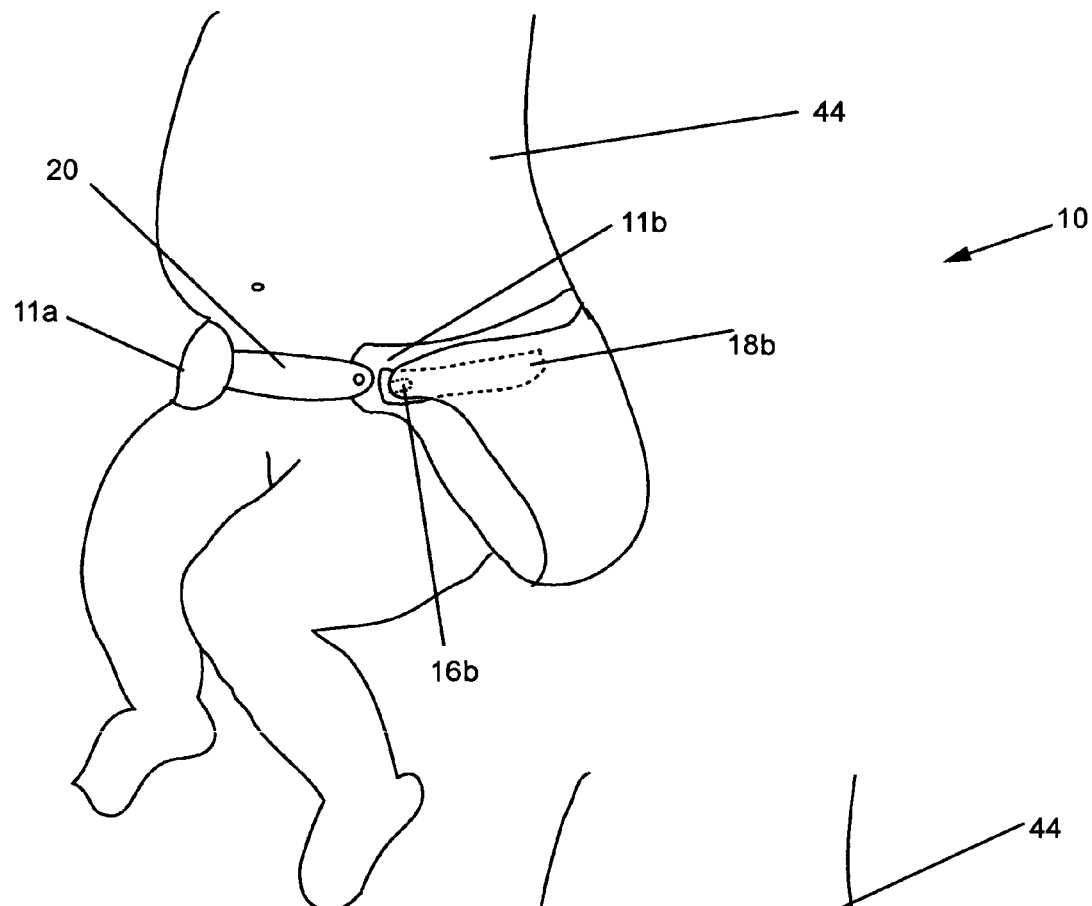
Figure 8B:
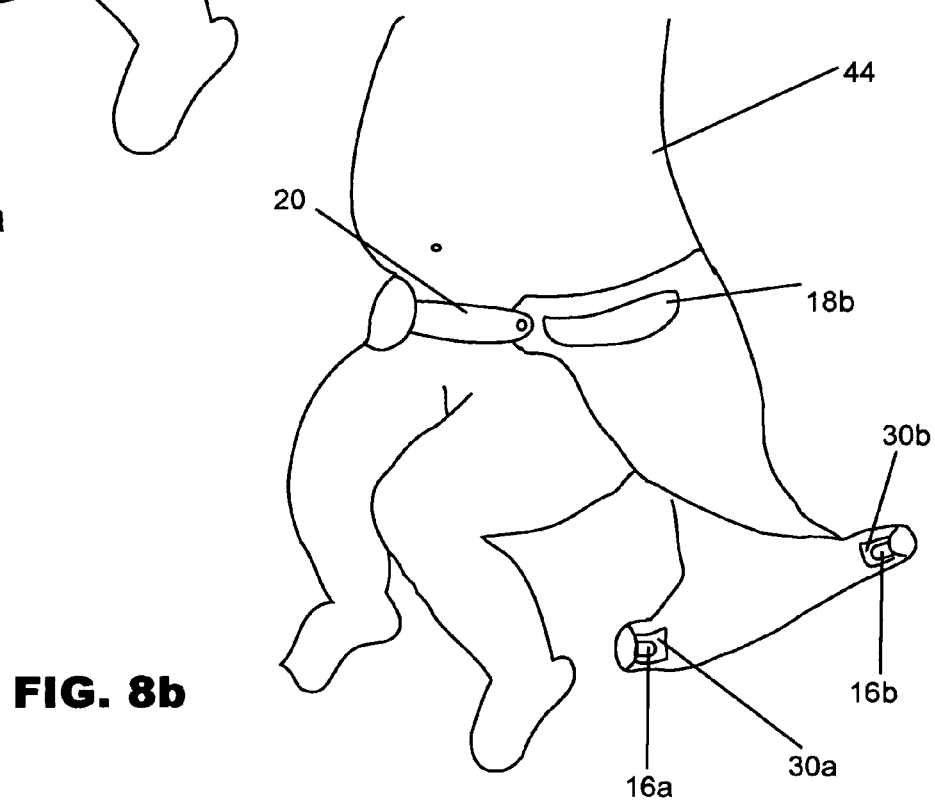
Figure 8C:
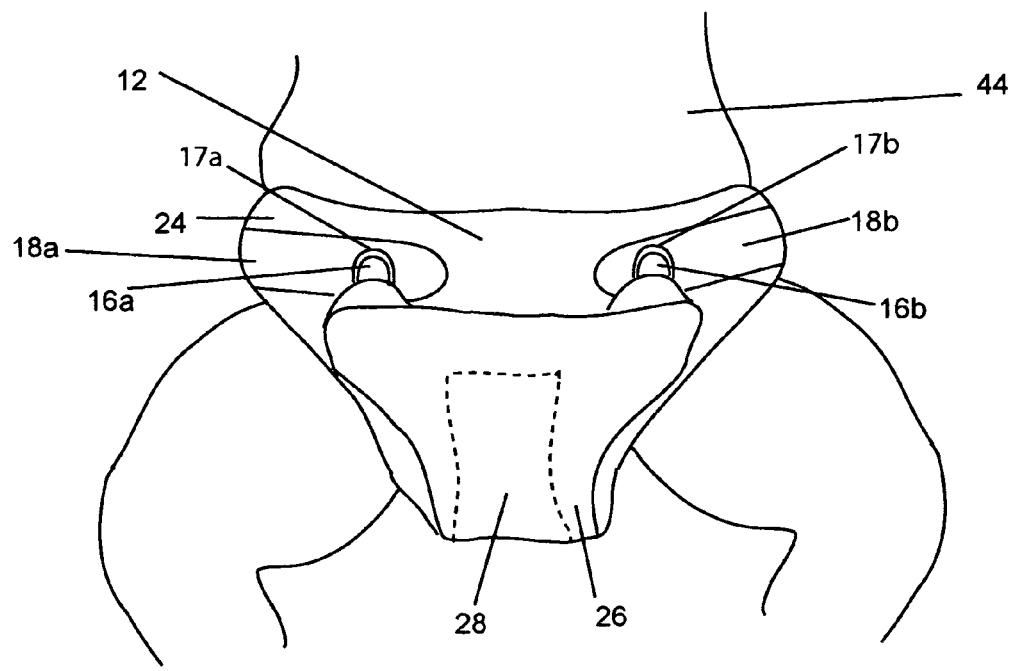
Figure 8D:
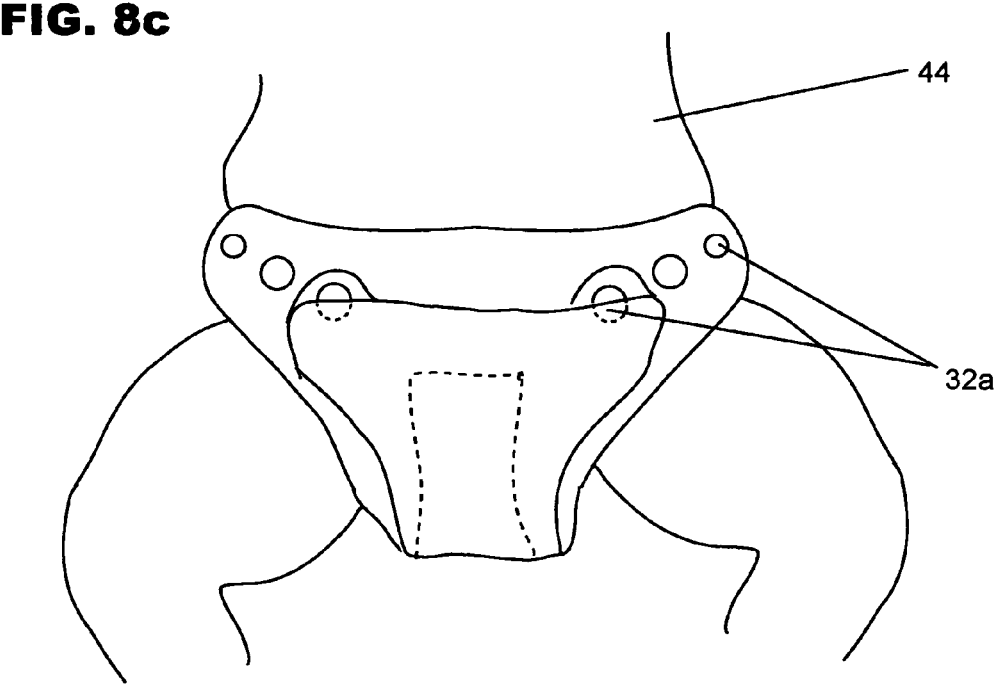

FIG. 7 shows an alternative embodiment of the belt 20. This belt 20 is an extension of the rear side flaps 11a, 11b. It is unitary with the rear portion. It is therefore not a separate element and does not need to be sewn on or have a separate pattern piece. It consists of the same material as the topsheet 26 and backsheet 24. The back caps of the snaps can be enclosed between the topsheet 26 and backsheet 24 so as they do not touch the babies skin. Though this belt may connect toward the center of the waist, it will not cause discomfort for the wearer since the connection device is small snap fasteners 32a, which are surrounded by soft material. There are no rough edges as is present with hook and loop fasteners.

Operation of Belt

In FIG. 7 another belt embodiment is shown. This belt 20 secures in around the waist region. The left side of the belt may be secured with two snaps to keep the extra ends from falling downward if set on the smallest setting. The belt may be made slightly larger than the waist on the largest setting so the pant can be pulled up and down like regular underwear if desired.

The aforementioned belts 20 are not meant to limit the invention. Other embodiments gentle on the waist of the child are conceivable. A belt with a tri glide buckle made of flexible material would also be possible, for instance.

Description of Hook Fasteners

Figure 9A:
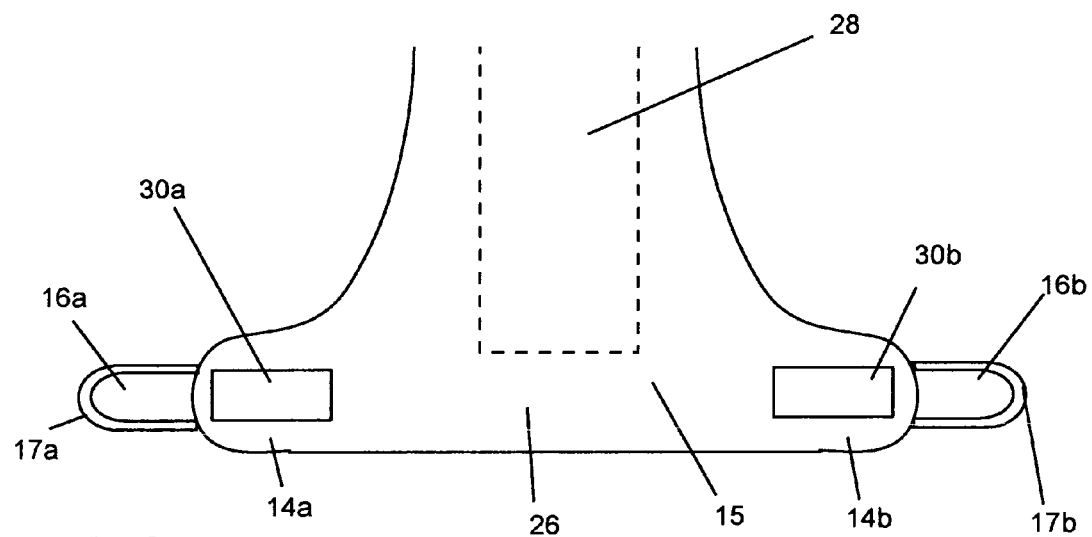

FIG. 9a shows a close up view of the hook fasteners 16a, 16b and the laundry securing tabs 30a, 30b. The hook fasteners are unique in that the inherently rough edges of hook material are encased in a binding material, such as bias tape. The hook binding material 17a, 17b surrounds the hook fastener 16a, 16b. WRIGHT'S double fold bias tape works well on this area. The laundry securing tabs 30a, 30b are sewn adjacent the hook tabs 16a, 16b.

This binding is inexpensive and keeps the dependent and caregiver safe from the rough edges of hook material. Additionally, it keeps hair and other debris that commonly gathers in hook material at a significant minimum. Besides being unsightly, gathered debris can compromise the refastening ability of hook and loop. It is also difficult and time consuming to pull out the hair and other debris. Also, unbound hook material has a greater chance of grasping onto clothing in the washing and drying cycle; possibly damaging delicate clothing items. Though people do use laundry tabs 30a, 30b (pieces of loop material sewn next to hook material) for the distinct purpose of securing hook before washing cloth diapers, they frequently become disengaged during the washing cycle. The binding, which encases the edges, helps protect the clothing. The binding also keeps the hook material from becoming tattered and worn looking on the ends. The above mentioned problems are significant disadvantages of using hook and loop material on cloth diapers, and the binding remedies these problems.

Figure 9B:
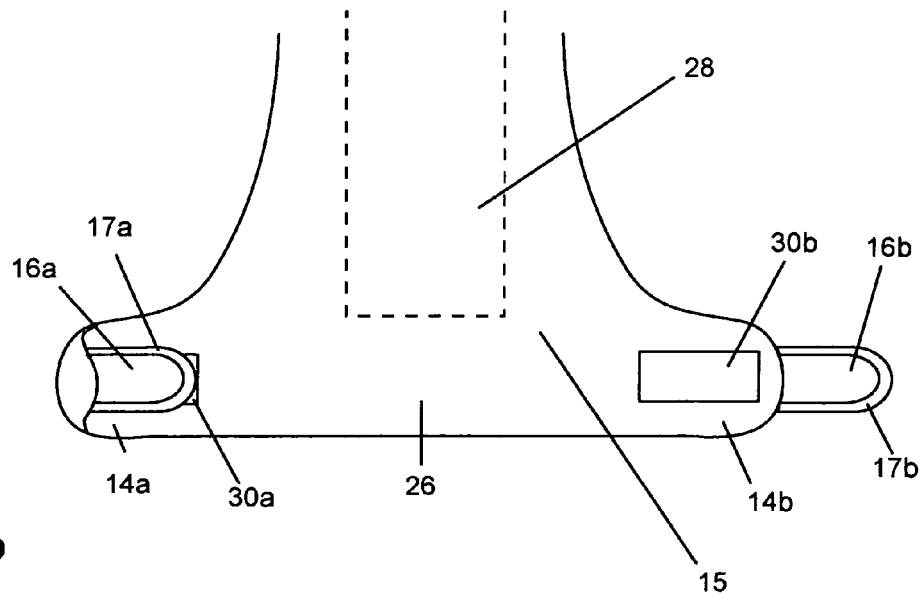

FIG. 9b shows a hook tab 16a in the secured position on a laundry securing tab 30a. The laundry securing tabs 30a, 30b are known on the art. Another use for them in this instance is to secure them in position when assisting an infant or helping a toddler use the bathroom facilities. If they are in secured position during these times, it will further keep the user away from all areas of the hook. Naturally, if a soft hook material is developed and on the market in the future, this will be a perfect embodiment for the invention.

Operation

Figure 1:
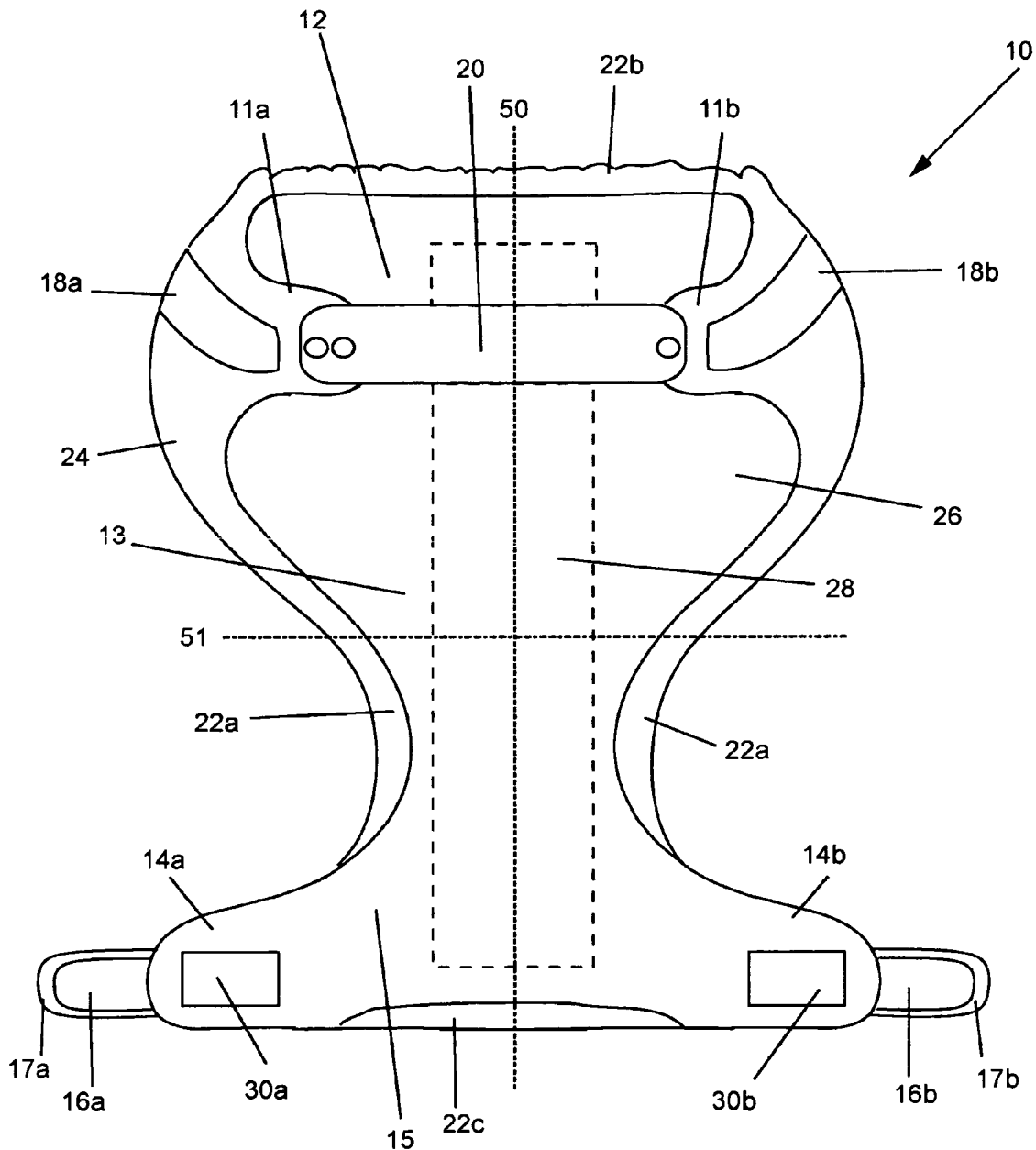
Figure 2A:
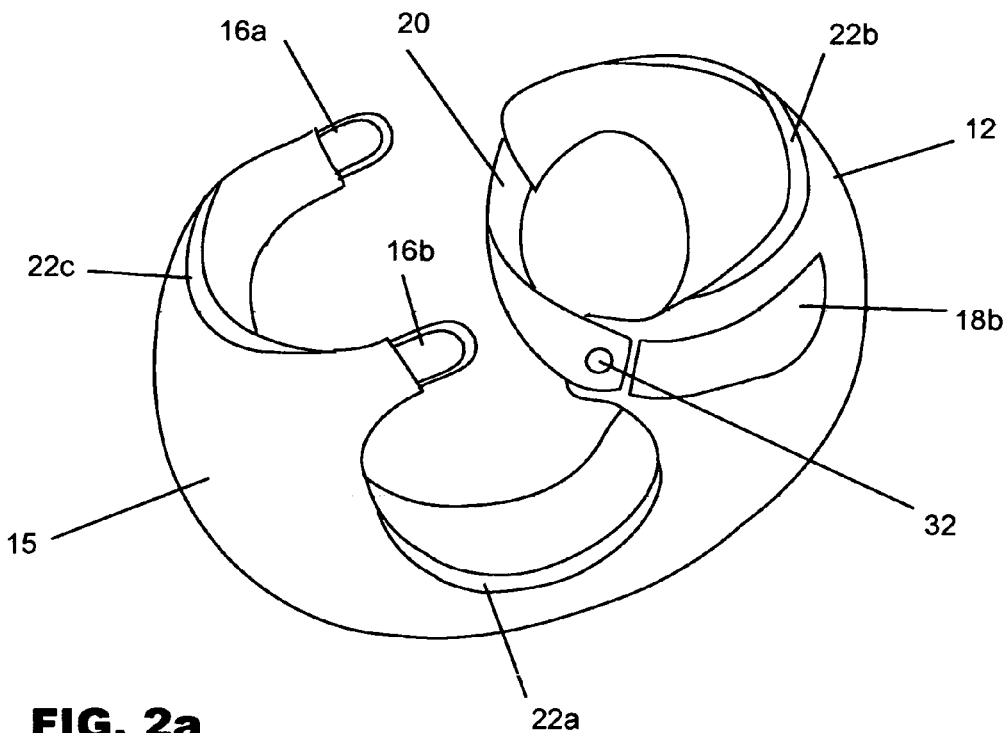
Figure 2B:
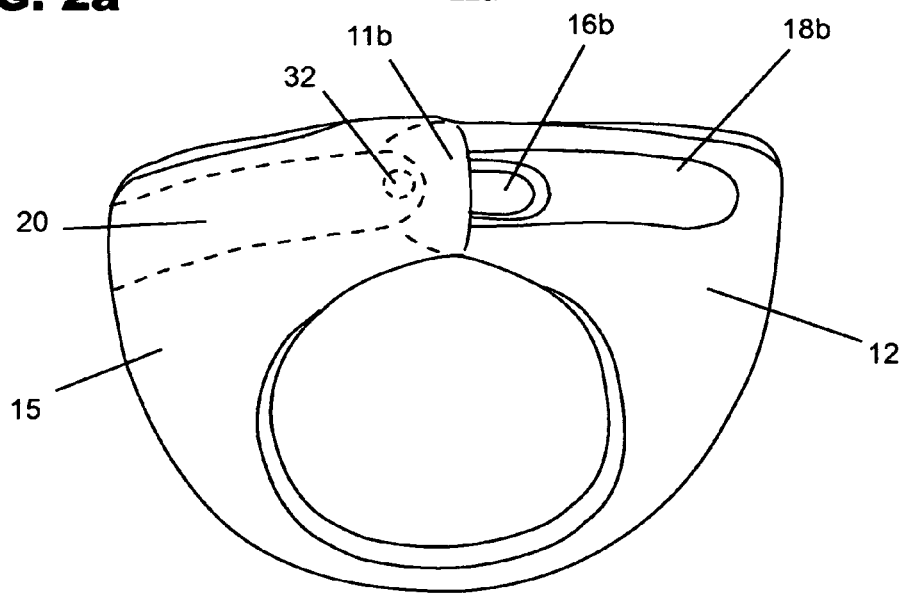
Figure 3A:
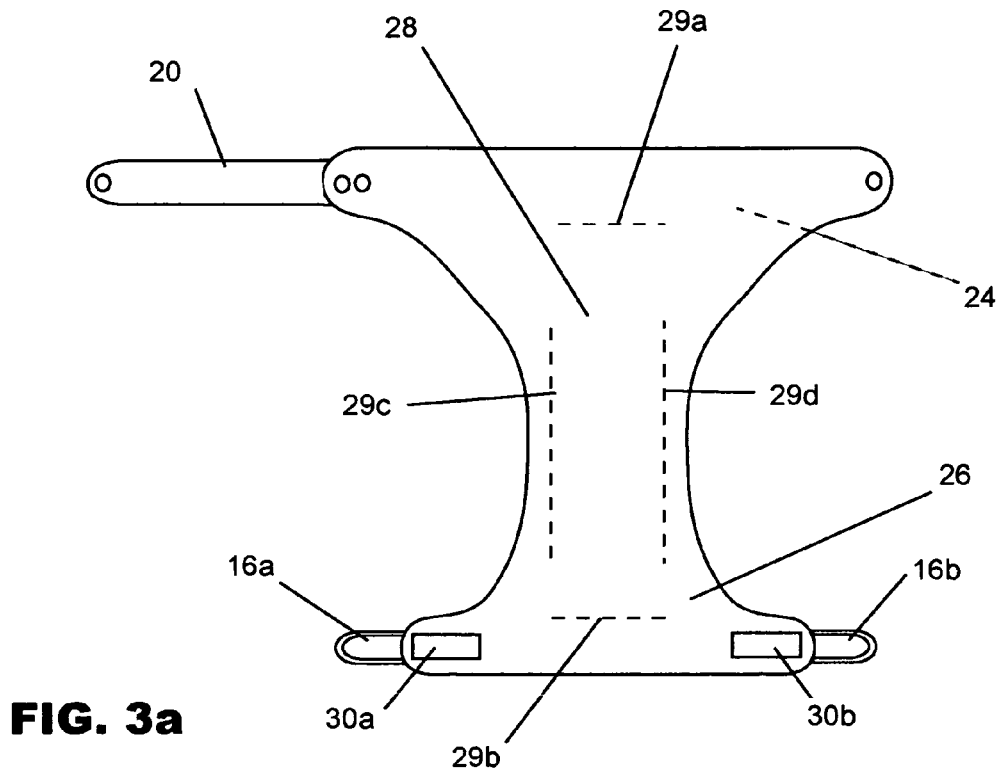
Figure 3B:
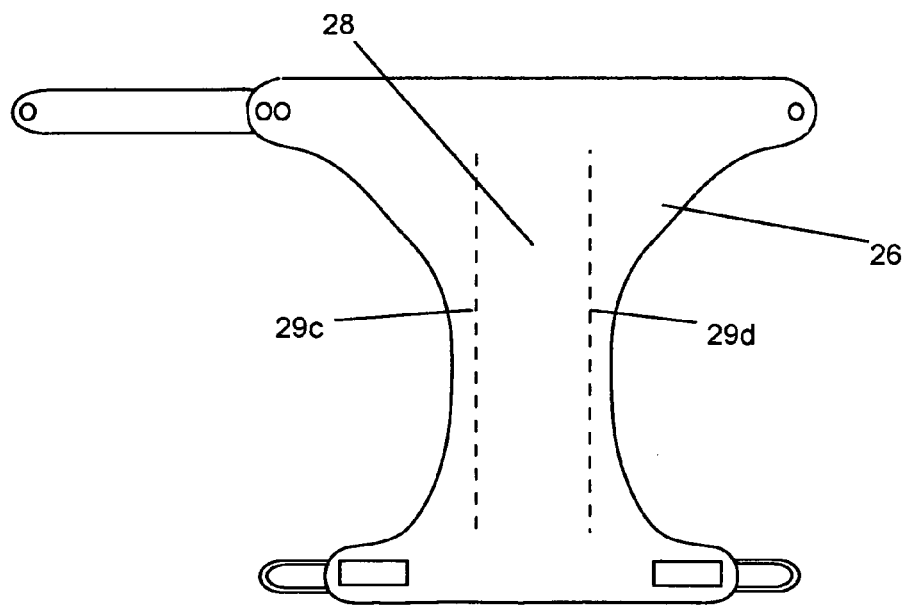
Figure 4A:
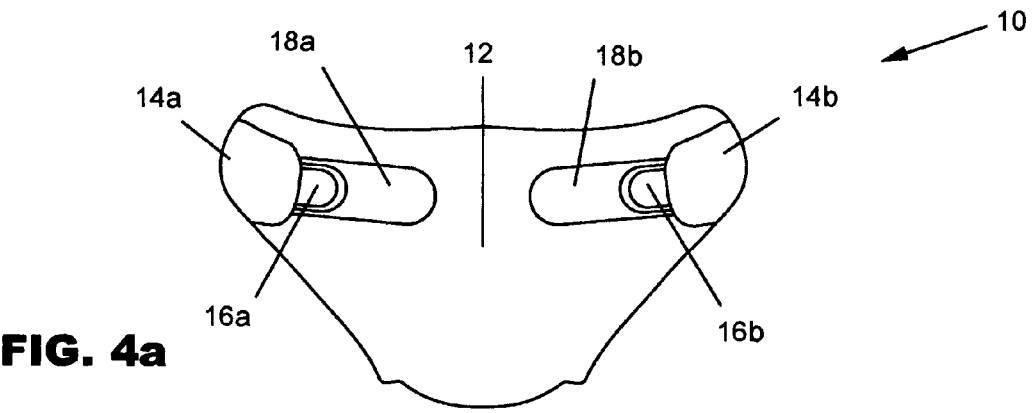
Figure 4B:
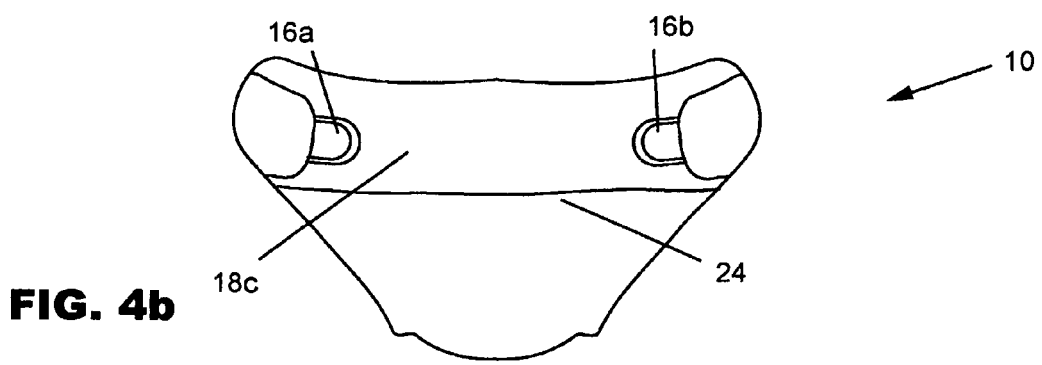
Figure 4C:
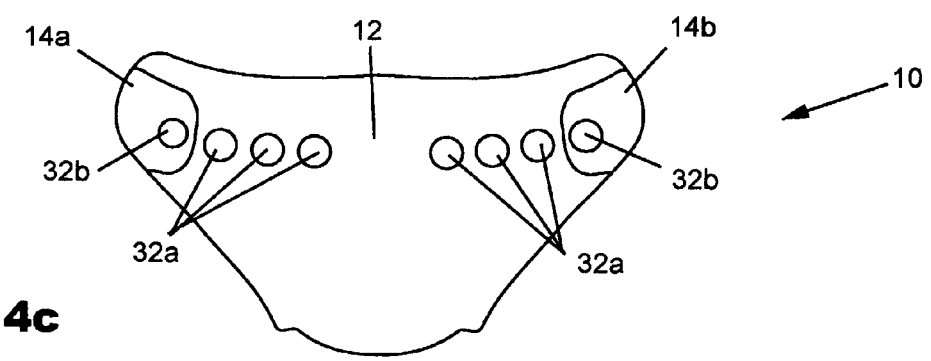
Figure 4D:
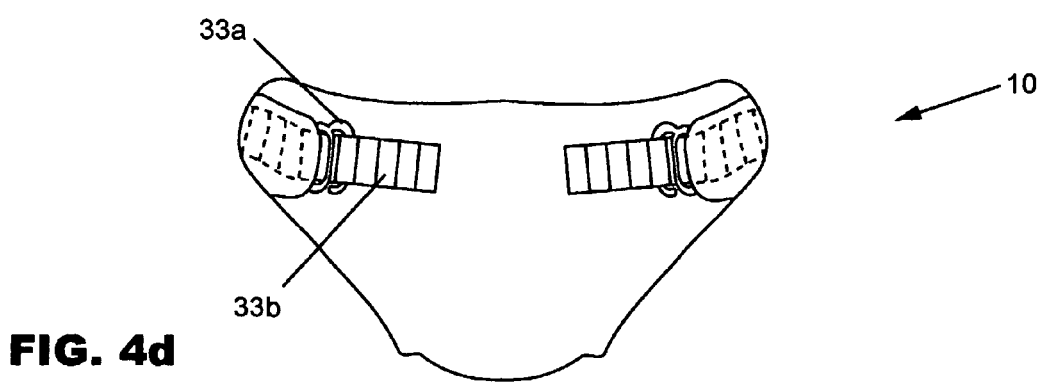
Figure 5A:
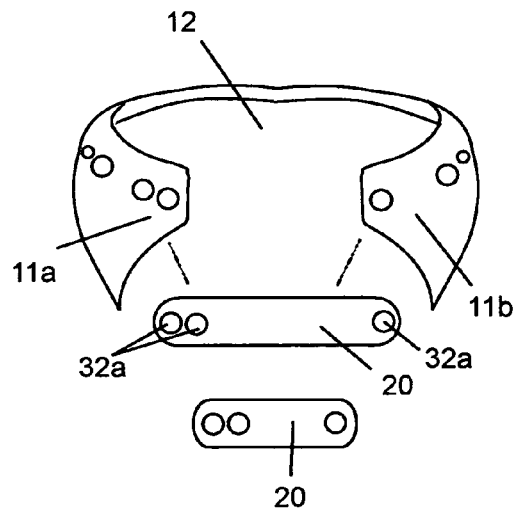
Figure 5B:
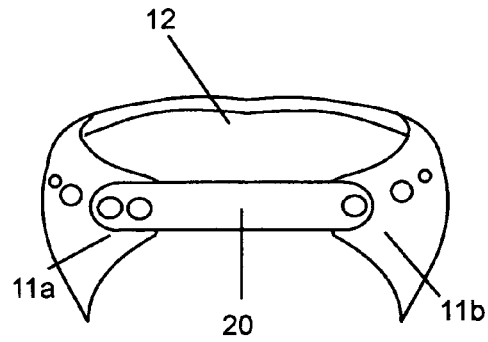
Figure 5C:
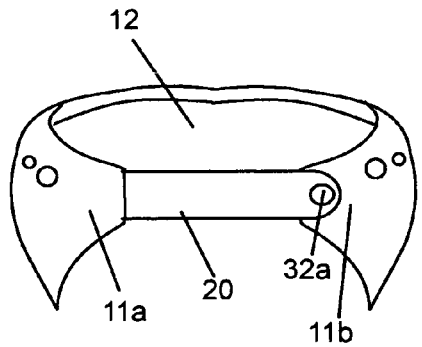

The hook fasteners which are attached to the elongated front side flaps 14a, 14b can be attached to the loop material 18a, 18b by being brought up between the legs of a user and attached to form a pant like shape. Depending on the waist size of the user, the hook fasteners 16a, 16b secure at the hips or rear of the wearer. FIG. 4a shows the hook fasteners 16a, 16b securing on the rear portion 12 of the wearer as would be the case with a person with a smaller waist. FIG. 2b shows a side view of a hook fastener 16b secured on receiving loop fastener 18b at the hip. By the fasteners being secured in the hip or rear regions the article assumes the shape of a complete pant, rather than the common loincloth style of belted garments with the likelihood of exposed hips.

Description of Embodiment with Removable Pads

Figure 10A:
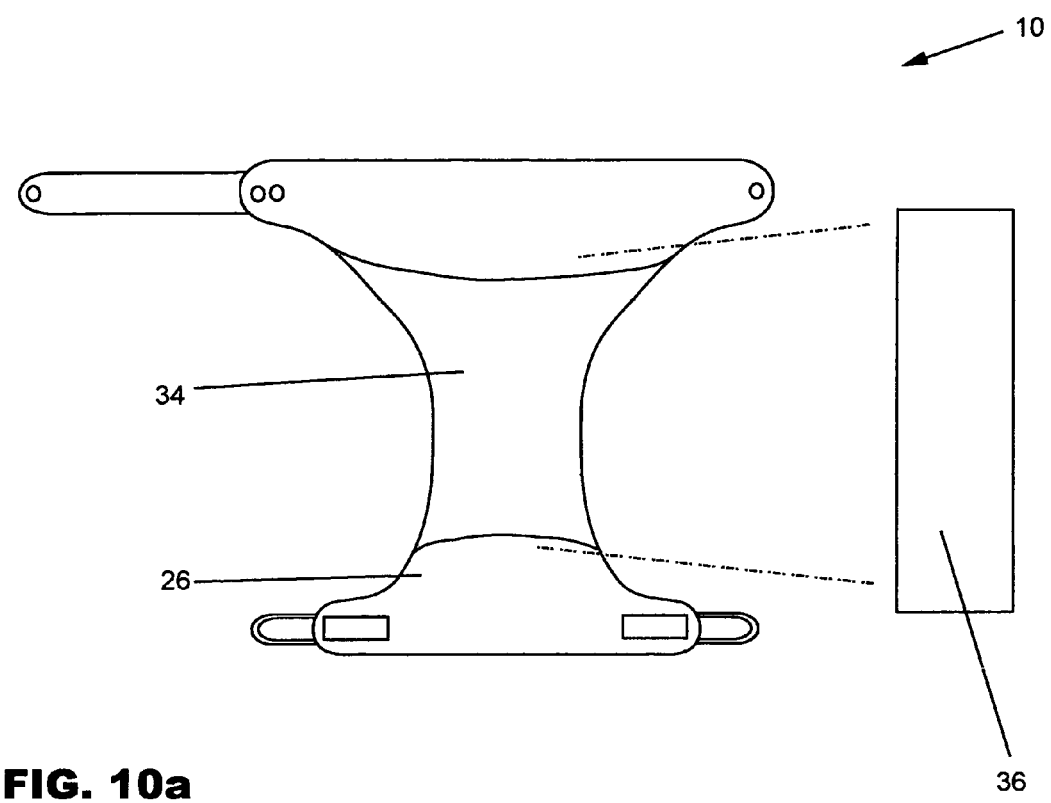

FIG. 10a shows an exploded front view of the absorbent article 10 with pocket sewn onto the topsheet 26. The unique pocket is only sewn along the left and right edge of the diaper. The top and bottom horizontal edges of the pocket are left open for the purpose of adding an external absorbent pad 36. The pocket can be constructed with the same material as the topsheet 26. The external absorbent pad 36 is shown next to the training pant 10 before it is inserted. The external absorbent pad 36 can be constructed with the same material as the internal absorbent soaker pad 28.

Figure 10B:
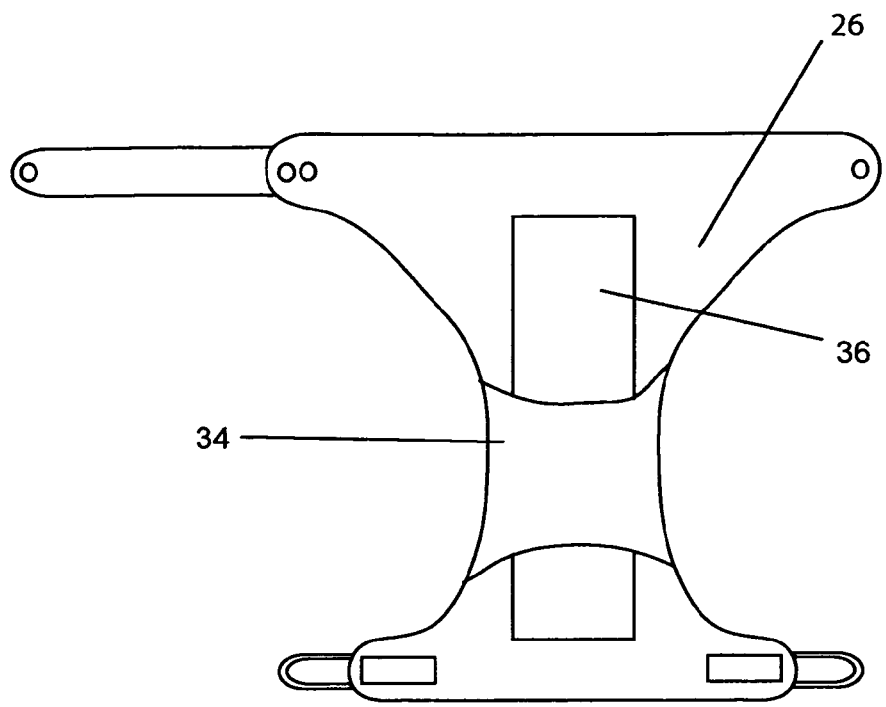
Figure 10C:
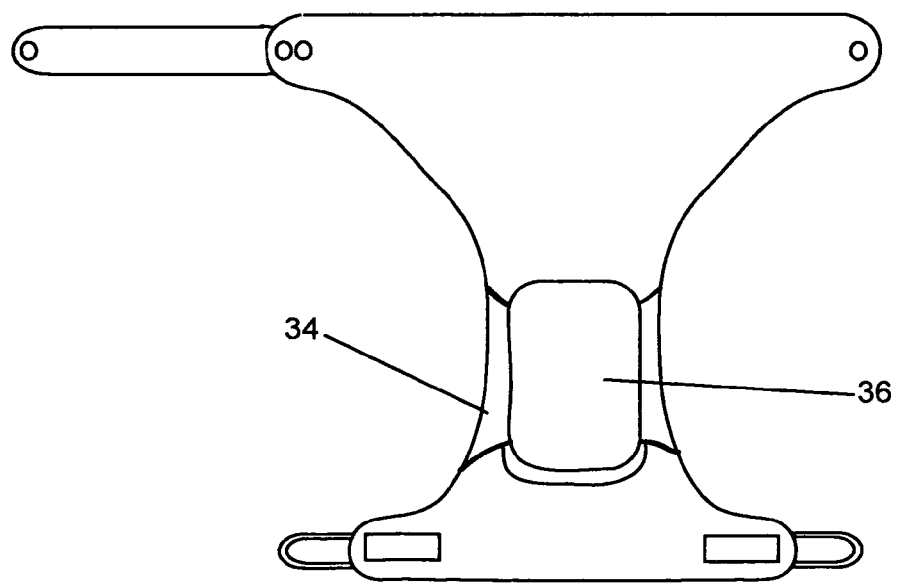

FIG. 10b shows a front view of the unique pocket 34 in a smaller size in relation to the topsheet 26 as compared with the drawing FIG. 10a. The external absorbent pad 36 is inserted in proper position FIG. 10c shows an additional way the external absorbent pad 36 can be placed in the pocket 34. The external absorbent pad 36 is folded over onto itself for additional absorbency.

Operation of Embodiments

In FIG. 10a an external soaker pad 36 is simply inserted at either open end of the pocket 34 at times when additional absorbency is desired. This would be very beneficial for times when heavier wetting is expected, such as at nighttime, long car rides, etc. By adding additional absorbency in this manner, the trimness of the diaper is not compromised at undue times. Also, as an external piece, the quick drying time of the absorbent garment is not compromised. This unique pocket 34, which is open on both ends, is very beneficial to a trim training pant. It is far easier to insert an absorbent pad 36 into a pocket that is open on both ends that doesn't run the entire length of the topsheet 26, especially in a training pant with a crotch that is thinner than a traditional diaper. This style pocket 34 will also allow a external absorbent pad 36 to loosen and come out in the laundry by itself, rather than having a caregiver remove a soiled external absorbent pad 36.

FIGS. 10b and 10c show the smaller size pocket 34 allows less material to be used which is beneficial in regards to cost savings. This smaller pocket 34 also allows the external absorbent pad 36 to be folded over onto itself, in effect doubling its absorbency. This is a novel way to add more absorbency in the critical areas without adding bulk to the rest of the training pant. It also allows the customer to purchase only one external absorbent pad 36 that can be used for different levels of absorbency, instead of buying multiple external pads of different absorbencies.

Description of Additional Embodiment of External Absorbent Pads

Figure 11:
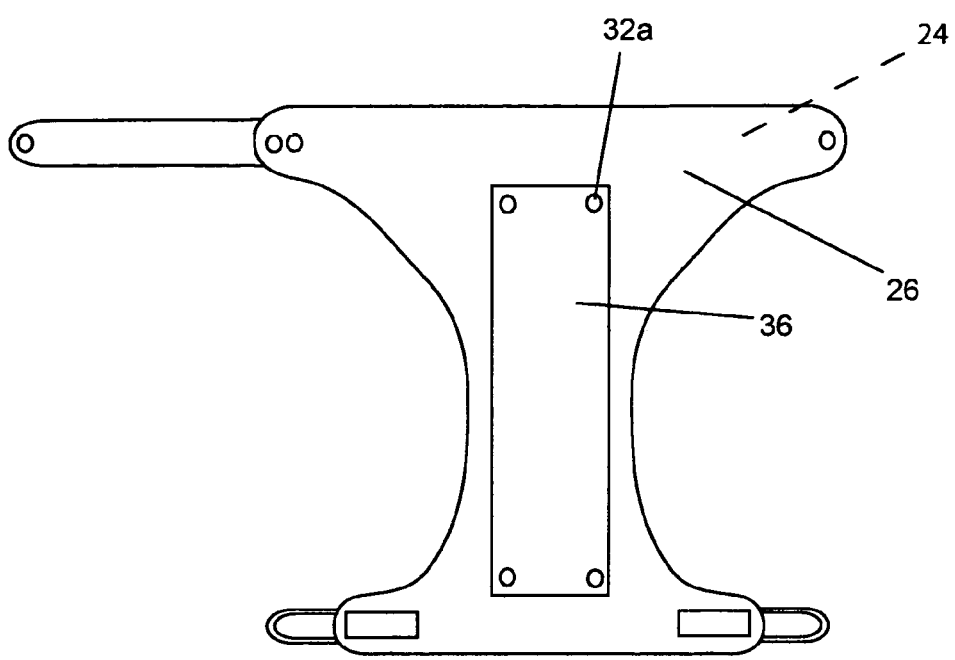

FIG. 11 shows an external absorbent pad 36 placed directly onto the topsheet 26 with snap fasteners 32a. The pad can be releasably attached when needed. The external absorbent pad 36 can be attached directly to the topsheet 26 with means other than snap fasteners and is not limited by these fasteners. Hook and loop for instance could attach the external absorbent pads 36 sufficiently. On the external soaker pad 36, the caps of the snap fasteners 32a can be hidden under the top layer by only being attached to the bottom layers before the external absorbent pad 36 is completely sewn together. The snaps attached to the topsheet 26 can also be hidden from the backsheet 24 of the training pant by securing the snaps to the topsheet 26 only with hidden fabric reinforcement.

Operation of Embodiment

In FIG. 11, an external absorbent pad 36 is simply snapped onto the topsheet 26 when needed. This is a relatively easy way to attach a pad without altering the sewing pattern or creating additional pattern pieces. Also, in the manner if an accident occurs which involves feces, the bottom snaps can be unsnapped and the external absorbent pad 36 can be submerged in the toilet without the entire body of the training pant being submerged. This is a more sanitary situation for the caregiver. Also, the external absorbent pad 36 does not need to be released from the snap fasteners 32a prior to washing. Since it is only secured on the ends it will wash and dry properly in the attached position.

Description of Additional Embodiment of External Absorbent Pads

Figure 12A:
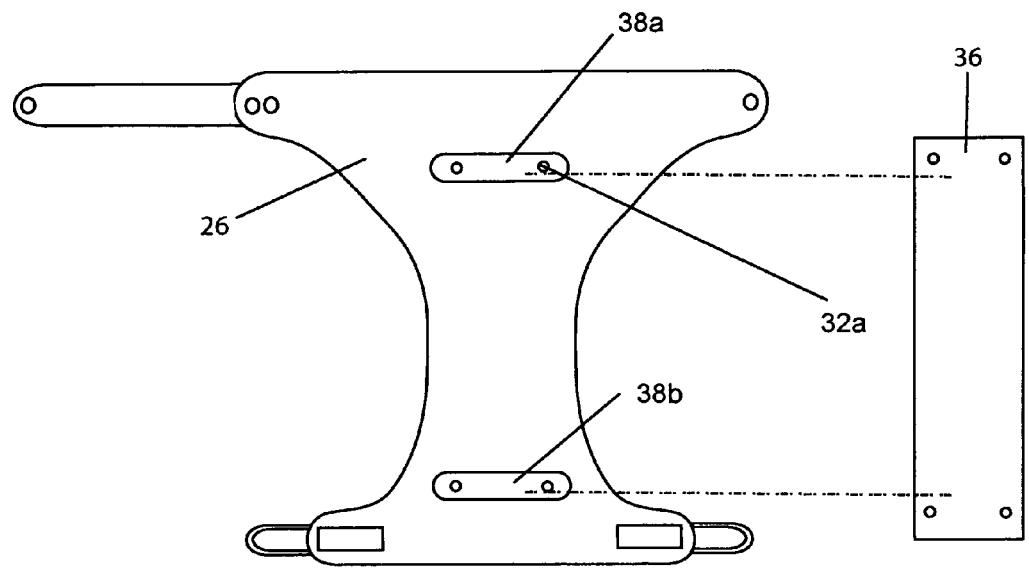
Figure 12B:
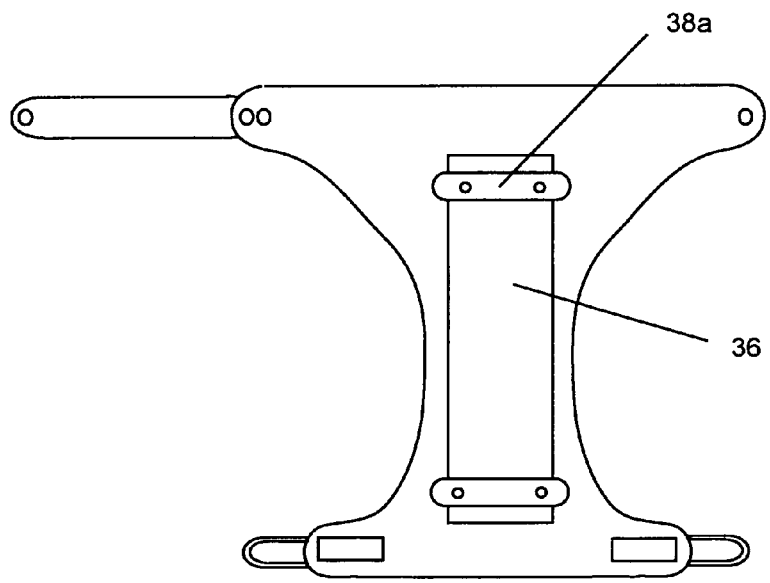

FIGS. 12a and 12b shows an external absorbent pad 36 that can be releasably attached to the topsheet 26 of the training pant with unique retaining bands 38a, 38b. These bands 38a, 38b can be made of soft elastic or be constructed of fabric with encased elastic. Additionally they can solely be constructed with fabric without the aid of elastic. A stretchy knit fabric would work well. The absorbent pad 36 can then be placed underneath the bands 38a, 38b to be held in place. With this construction, a caregiver could insert their own fabric to be used as an additional soaker pad. For instance they could fold a soft washcloth into thirds and tuck the edges underneath the retaining bands 38a, 38b. These retaining bands 38a, 38b could also be provided with snaps so they could also use an external absorbent pad 36 that could snap in if they prefer the additional security of snap fasteners. Additionally, both a pad could be tucked underneath the retaining bands 38a, 38b and snapped to the top of the retaining bands 38a, 38b for times when super absorbency is needed.

Operation of Embodiment

The external absorbent pad 36 is simply tucked under the retaining bands when needed. This can easily be removed in the wash without the aid of human hands. Additionally, if the embodiment is supplied with snaps to the inner or outer surface of the retaining bands, an additional snap in style external absorbent pad 36 can be used. This can be used with or without another external pad provided by the customer. The snapped in pad does not need to be unattached before washing to get sufficiently clean.

Description of Embodiment of Training Pant with No Internal Soaker or Topsheet

Figure 13:
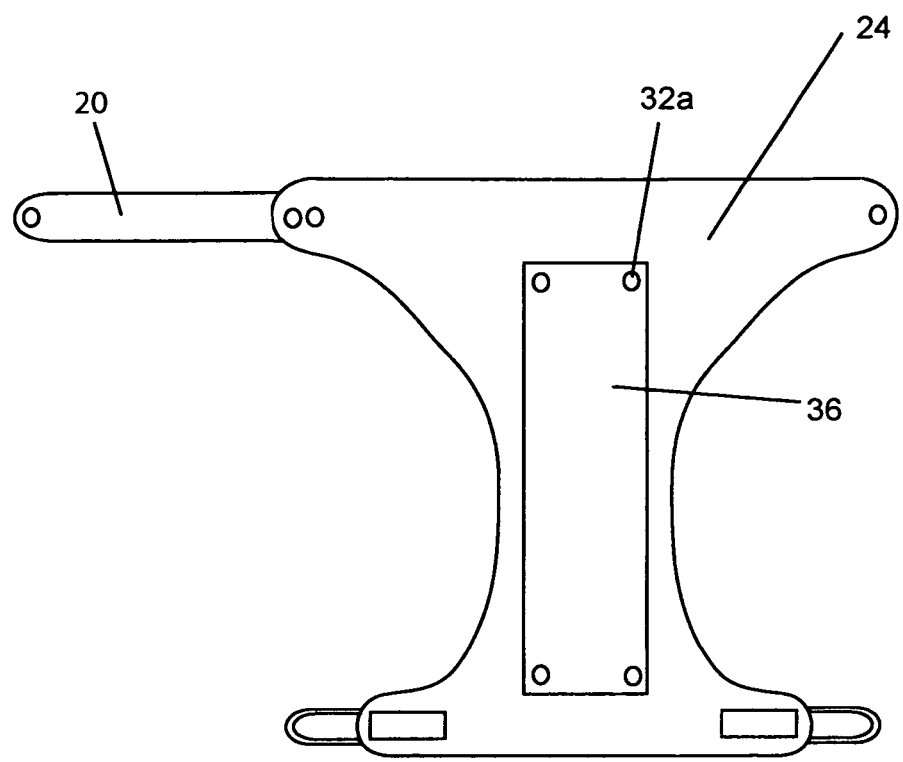

FIG. 13 shows an embodiment of the training pant which does not consist of a topsheet 26, a backsheet 24, and an absorbent soaker pad 28 sandwiched therebetween. Instead, the article is constructed with a water impermeable backsheet 24 and an external absorbent pad 36. The structure of the article can be constructed exactly as described in previous embodiments besides the lack of topsheet 26 and internal absorbent soaker pad 28. The external absorbent pad 36 can be releasably secured on the backsheet by methods described heretofore; snaps fasteners 32a, retaining bands 38a, 38b as shown in FIGS. 12a and 12b, etc. Other methods of attaching the external absorbent pad 36 are also in the scope of the invention.

Operation of Embodiment

Attach an external absorbent pad 36 to the backsheet 24 fasteners. Then secure the belt 20. Bring the suspended front portion 15 between the legs and secure with fastening mechanisms to the rear portion 12 as described in the aforementioned embodiments. If an accident consisting of only urine occurs, then the pad can be replaced without having to change rest of the absorbent article. The water impermeable backsheet 24 can simply be wiped down if necessary. This would more affordable for customers since they would only have to buy an abundance of external absorbent pads 36, rather than an abundance of absorbent articles. Of course, with less materials and pattern pieces, it is easier and therefore cheaper to manufacture.

Description of Embodiment with Pant Legs

FIG. 14a shows a front view of this unique embodiment of an absorbent article that includes trouser type pant legs 40. Essentially, the rear portion of the absorbent article 12 is permanently affixed to pants with a cut out crotch region. FIG. 14a shows the absorbent article 10 with the rear portion 12 affixed to the open crotch pants 40. The front portion 15 is in an unsecured state in this illustration; it is suspended between the legs. The open crotch pants 40 can be made of any comfortable material. The crotch opening can be serged, bound with edging material, or sewn down on open edges to keep the edges from unraveling. Additionally, elastic can be added to open crotch area edges to keep the open crotch area securely away from the genitalia. Fold over elastic can be used as well. FIG. 14b shows a front view of the absorbent article with legs in a fully secured state. FIG. 14c shows the absorbent article from the backview in a secured state. The absorbent article 10 used over the open crotch pants 40 can be any embodiment previously described. Additionally, the belt can be foregone in an embodiment with the open crotch pants 40 as the adjustable waist elastic on the open crotch pants 40 could suffice. It is important to note that the sizing of the absorbent article before it is adhered to the pants should remain in accordance to the predetermined grading as though the article were not secured on the open crotch pants. That way the sizing will be identical whether the customer purchases the absorbent article alone, attached to open crotch pants or to open crotch shorts. This will aid in ease of manufacturing and ease of sizing for the customer.

Operation of Embodiment

Slide the open crotch pants 40 over the child's legs with the front portion 15 of the absorbent article left unsecured from the back portion 12. Once the open crotch pants 40 are around the waist of the dependent, flip the front portion 15, which is suspended between the legs, up to the abdomen region of the baby. Secure the hook fastener 16a, 16b to the loop fastener 18a, 18b on the backsheet 24 of the absorbent article 10. Of course if the embodiment is supplied with snap fasteners or other mechanical fasteners, secure those as required for releasable attachment.

This embodiment is valuable for times when weather requires warmer articles of clothing. In this embodiment, no additional article of clothing need to be placed on top of the absorbent article. This keeps the crotch region easily accessible for times when using the bathroom is desired. The front portion 15 is simply releasably detached from the backsheet 24 and brought down between the legs near the rear. The front portion 15 can then be releasably secured to the backsheet with the genitals exposed if desired. Or the laundry tabs securing tabs 30a, 30b can be employed if desired to keep the hook fasteners 16a, 16b away from the child's skin. This embodiment would work particularly well with the embodiment described in FIG. 13; whereas the absorbent article affixed to the open crotch pants 40 consisted of a backsheet 24 and external absorbent pad 36. That way, only the external absorbent pad 36 would need to be exchanged if an accident occurred. The legs of the embodiment can of course be cut to the length of shorts.

Figure 15:
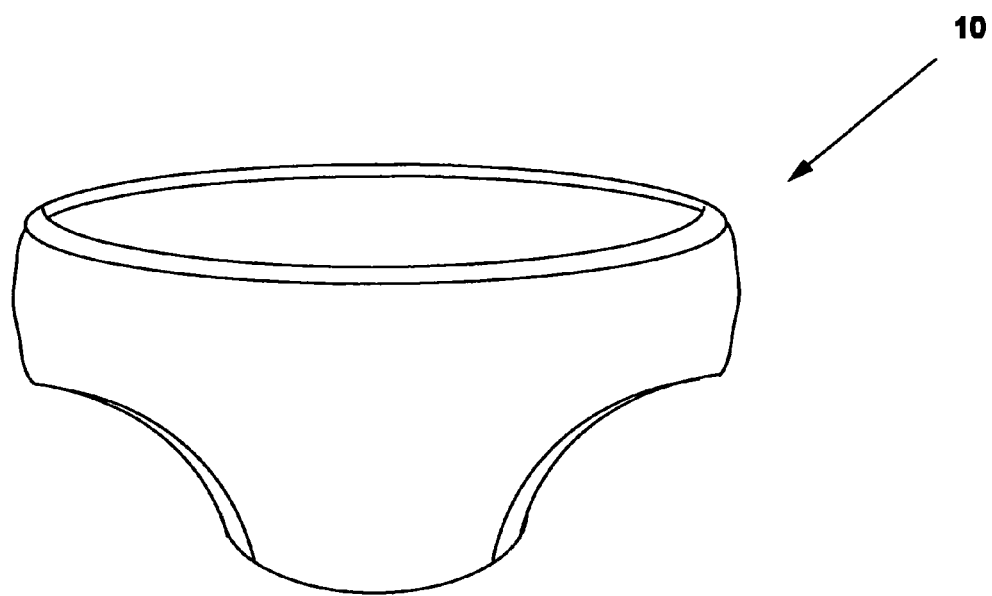

FIG. 15 shows the absorbent article in a front view fastened state.

CONCLUSIONS, RAMIFICATIONS, AND SCOPE OF INVENTION

Thus the reader will see that the embodiments described herein solve the aforementioned problems. By providing an absorbent article which has a front portion that can be flipped down and secured away from the genitals while remaining secured on the waist of the child, the absorbent article succeeds in making it quicker and easier for a caregiver to assist a child from infant to toddlerhood in using the bathroom. The absorbent article provides a comfortable alternative to other belted garments by providing hook and loop only in designated areas away from the abdomen, and by keeping all sharp areas of hook encased in binding material. Other embodiments which forgo hook and loop entirely supply additional comfort options. By creating an article out of reusable, washable, more skin friendly materials even more comfort is gained, as well as the important aspect of creating an environmentally sound product, which is important to Elimination Communication practitioners'. Additionally, providing an absorbent article of this type that can be reused, the product is less expensive than alternatives. The washable apparel materials combined with the construction that attaches the front portion to the back portion and does not leave the hips exposed in a loincloth fashion, achieves in providing a socially acceptable, non-embarrassing, yet functional garment.

The aforesaid construction regarding the frontal to back panel construction attachment also lends itself to easier adornment at various ages, stages and positions, keeping the child and caregiver happier.

Also, as the product can be used as a belted garment or pull up underwear style garment, said article also succeeds in providing a product that can be used for different stages of growth and development. This will help the product 'grow' with the child and not necessitate the purchase of separate items for different stages.

Additionally, by providing a belt plus a front portion that is highly adjustable, the article achieves better fit than most belted diapers, which directly relates to keeping excrement from leaking when accidents occur. It also lends to fitting a wider size range of persons.

By supplying additional external soaker pads with the ability to releasably attach, leaking is even less likely and the caregiver can feel confident using the absorbent article in any occasion without having to purchase separate articles for heavier wetting times. The unique external soaker pads previously described aid in keeping the article trim, absorbent and easier to care for than other washable absorbent garments.

To provide an article which can keep a child warm without sacrificing the ability to access the genitals quickly for bodily releases, is uniquely achieved by permanently adhering the absorbent article to the backside of open crotch pants. The importance of this embodiment is not to be underestimated. Caregivers can finally go into public with their children without worry of undressing many layers and without embarrassment.

And finally, the article achieves ease of laundry care by providing a unique method of sewing in the internal soaker pads, by providing external soaker pads to keep the article drying quickly even with a great deal of absorbency, and by providing external soakers which do not need to be handled after they are soiled because they will work themselves out in the wash or can remain adhered. Also, with hook binding materials provided, ease of care is even greater because the unique construction helps keep lint, hair and other debris out of the attachment areas and helps prevent securement onto delicate clothing.

While the above description contains many specificities, these should not be construed as limitations on the scope of the invention, but rather as an exemplification of the embodiments thereof. Many other variations are possible. For example, the belt could be made to permanently affixed to one rear wing and be made to releasably attach to the other with just one snap. The belt could conceivably be made to detachably secure with hook material, provided the hook material was bound and only attached on at least one lateral end. The belt could also be made with buttonhole elastic. This is an elastic band with slits spaced at fixed intervals for the purpose of button attachment. The button could be permanently attached at a predetermined point on a rear side flap. The belt could also be made with adjustable loop type means, similar to that of a bra strap.

Also, an additional body piece of material the identical size to the topsheet and backsheet could be sewn between the topsheet and backsheet. This could be a water resistant material. That way the topsheet and backsheet could both be any non-waterproof material, yet the absorbent article would still possess waterproofing abilities. This is beneficial because waterproof materials are significantly more limited than water permeable materials. There are many more kid friendly prints, colors, and textures available in water pervious materials. Another embodiment would provide a narrow waterproofing strip of material that runs the length of the crotch region between the topsheet and backsheet. This would help with waterproofing, yet keep the article cooler in warm weather since waterproof material tends to be less breathable than its counterpart.

A belted diaper could also be constructed in a cheaper to produce, more underwear like fashion. It could consist of one body layer with a small absorbent pad sewn into the crotch region. The belt could be integral so only two pattern pieces need to be used; the body layer and the absorbent pad layer. This would be a cheaper alternative and great for children who are mostly potty trained, yet still have a minimal amount of accidents.

The article could also easily be made as a one size absorbent article. The waist has enough adjustability to fit birth to toddler sizes. The body could be adjusted to accommodate these sizes with snap fasteners, folding or other means.

Though these embodiments have mostly been described with potty learning children as its focus, the absorbent article would also be beneficial for use in incontinent adults.

Accordingly, the scope of the invention should be determined not by the embodiments illustrated, but by the appended claims and their legal equivalents.

REFERENCE NUMERALS 10 absorbent article
11a elongated rear side flap (left)
11b elongated rear side flap (right)
12 rear portion
13 crotch portion
14a elongated front side flap (left)
14b elongated front side flap (right)
15 front portion
16a hook fastener (left)
16b hook fastener (right)
17a hook binding (left)
17b hook binding (right)
18a loop fastener (left)
18b loop fastener (right)
18c continuous loop fastener material
20 adjustable waist attachment component, belt
22a leg elastic
22b rear elastic
22c front elastic
24 backsheet
26 topsheet
28 absorbent soaker pad
29a absorbent pad top horizontal edge
29b absorbent pad bottom horizontal edge
28c absorbent pad left vertical edge
29d absorbent pad right vertical edge
30a laundry securing tab (left)
30b laundry securing tab (right)
32a snap fasteners
32b male, or stud snap fasteners
32c socket, or female snap fasteners
32d fastener cap
33a s hook
33b s hook receivers
34a pocket
34b smaller pocket
36 external absorbent pad
38a retaining band (top)
38b retaining band (bottom)
40 open crotch pants
42 legs
44 body
46 open crotch area

The invention claimed is:

1. A washable, reusable, absorbent article comprising:
a front portion, a rear portion and a crotch portion therebetween;
an absorbent core;
a front waist edge, a back waist edge and edges that define a leg opening therebetween;
a releasable belt comprising two distal ends;
a longitudinal direction that runs substantially parallel to the lengthwise direction of said crotch portion and a latitudinal direction that runs substantially perpendicular to the longitudinal direction of said crotch portion;
an inner surface adapted for contact with a wearers body and an outer surface, opposite said inner surface;
said front portion further comprising laterally extended side flaps at said front waist edge and tapering substantially to said crotch portion;
said front portion side flaps further comprising front portion side flap fasteners;
said rear portion further comprising laterally extended side flaps at said rear waist edge and tapering substantially to said crotch portion;
said rear portion side flaps further comprising distal ends;
said rear portion side flaps further comprising belt fasteners to attach said releasable belt;
said belt fasteners located adjacent to said distal ends of said rear portion side flaps;

said releasable belt comprising distal end fasteners on both distal ends of said releasable belt adapted to attach to each of said rear portion side flap belt fasteners;

said releasable belt constructed without fastening means for said front portion engagement wherein said front portion is only adapted to attach to said rear portion;

said rear portion further comprising a set of fasteners for receiving said front portion side flaps fasteners;

said set of fasteners for receiving said front portion side flaps fasteners disposed inboard of said belt fasteners in said latitudinal direction;

whereby when said absorbent article is worn by a user said front portion side flaps extend past and effectively cover said belt and overlap said rear portion side flaps in such a way that said article will assume a pant like shape;

whereby said front portion does not attach to said belt, thus said front portion and said back portion adjust to fit independently of said belt, allowing transformation of the article from a belted garment ideal for toileting without removing said article to a garment ideal for pulling up and down over the legs like a traditional training pant by removing said belt.

2. An absorbent article as claimed in claim 1, including a pocket with an opening on the top horizontal edge of said pocket and an opening on the bottom horizontal edge of said pocket.

3. An absorbent article as claimed in claim 1, further including an external absorbent pad attached by means comprising snap fasteners, retaining bands, or washable hook and loop, whereby additional absorbency is achieved without compromising drying times.

4. An absorbent article as claimed in claim 1, wherein said front portion and said rear portion fasteners comprise washable hook and loop material, snap fasteners, s hooks, or the like.

5. An absorbent article as claimed in claim 1, wherein said belt is provided with snaps that can releasably secure to fold said belt over onto itself whereby said belt shortens in length and is further provided with an additional snap fastener on the folded end which can releasably attach to said rear portion side flap belt fastener.

6. An absorbent article as claimed in claim 1, wherein fasteners on said belt are comprised of snap fasteners, and one distal edge of said belt contains two snaps adjacent each other that attach to two corresponding receiving fasteners on said rear portion side flap whereby said two adjacent snaps prevent said belt from rotating when trying to secure the opposite end of said belt to opposite said rear portion side flap fastener.

7. An absorbent article as claimed in claim 1, wherein said fasteners that are attached to said front portion side flaps comprise hook material wherein said hook material is provided with encasing material to bind all exposed edges by attaching bias tape or the like around the front and back edges of said hook fasteners thereby preventing said hook fasteners from scratching the user or caregiver.

8. An absorbent article as claimed in claim 1, wherein said fasteners that are attached to said front portion and said rear portion comprise snap fasteners.

9. An absorbent article as claimed in claim 1, further including open crotch pants or split crotch pants or shorts.

10. An absorbent article as claimed in claim 1, further including retaining bands on said inner surface for holding external absorbent pads in place.

11. An absorbent article as claimed in claim 1, wherein said belt is shorter in length than said rear portion waist edge length.

12. An absorbent article as claimed in claim 1, wherein said belt is shorter in length than said front portion waist edge.

13. An absorbent article as claimed in claim 1, wherein said absorbent core disposable.

14. An absorbent article as claimed in claim 1, wherein said rear portion fasteners for front portion engagement start adjacent one said belt fastener and continue latitudinally to end adjacent said opposing belt fastener.

15. An washable, reusable, absorbent article comprising:
a front portion, a rear portion and a crotch portion therebetween;
an absorbent core;
a front waist edge, a back waist edge and edges that define a leg opening therebetween;
a releasable belt comprising two distal ends;
an inside surface adapted for contact with a wearers body and an outside surface opposite said inside surface;
a longitudinal direction that runs substantially parallel to the lengthwise direction of said crotch portion and a latitudinal direction that runs substantially perpendicular to the longitudinal direction of said crotch portion;
said front portion further comprising laterally extended side flaps at said front waist edge and tapering substantially to said crotch portion;
said front portion side flaps further comprising front portion side flap fasteners;
said rear portion further comprising laterally extended side flaps at said rear waist edge and tapering substantially to said crotch portion;
said rear portion side flaps further comprising distal ends;
one said rear portion side flap further comprising a releasable belt fastener disposed adjacent to said distal end;
said releasable belt comprising distal ends wherein a fastener on one said distal end is adapted to attach to said rear portion side flap belt fastener and the opposing said distal end of said belt is permanently attached to opposing said rear portion side flap;
said releasable belt constructed without fastening means for said front portion engagement wherein said front portion is only adapted to attach to said rear portion;
said rear portion further comprising a set of fasteners for receiving said front portion side flaps fasteners;
said set of fasteners for receiving said front portion side flap fasteners disposed inboard of said belt fastener and said distal end of opposing said rear portion side flap, in said latitudinal direction;
whereby when said absorbent article is worn by a user said front portion side flaps extend past and effectively cover said belt and overlap said rear portion side flaps in such a way that said article will assume a pant like shape;
whereby said front portion does not attach to said belt, thus said front portion and said back portion adjust to fit independently of said belt, allowing transformation of said article from a belted garment ideal for toileting without removing said article to a garment ideal for pulling up and down over the legs like a traditional training pant by adjusting said belt.

16. An absorbent article as claimed in claim 15, wherein said absorbent core is disposable.

17. An absorbent article as claimed in claim 15, wherein said rear portion fasteners for front portion engagement start adjacent one said belt fastener on said rear portion side flap and continue latitudinally to end adjacent said opposing distal edge of said rear portion side flap.

18. A method of using the absorbent article of claim 1 comprising:

placing said rear portion against the rear waist region of the user covering the buttocks;

fastening to said belt fasteners said refastenable belt that is situated only on the front waist portion between said rear portion side flaps, said belt acting as a connector to said rear portion side flaps hence enabling said rear portion to encircle the waist of the user;

drawing said front portion through the crotch area between the legs of the user;

attaching said front portion, which is supplied with fasteners on said front portion side flaps, by pulling said front portion up to the front waistline of the user and stretching both said fasteners in opposing directions covering and going past the left and right said distal edges of said belt and continuing to the left and right hip regions of the user overlapping said rear portion side flaps and engaging said fasteners disposed inboard of said belt fasteners in a latitudinal direction on said rear portion;

removing said belt when a pull up style absorbent garment is desired;

leaving said waist belt fastened when a belted configuration is desired;

whereby said belt of said absorbent article can be adjusted or removed according to the desired type of absorbent article needed, such as a belted or conventional pull up.

19. The method of claim 18, comprising pulling over the legs of the user open crotch pants or split crotch pants or shorts that are underneath said absorbent article by having said rear portion of said absorbent article attached on top of the outer rear portion of said pants and then pulling said front portion of said absorbent article under the legs over on top of said pants and then attaching said front portion, which is supplied with said fasteners on opposing said side flaps, by pulling said front portion up to the front waistline of the user and stretching both said fasteners in opposing directions covering the front of said pants and continuing to the left and right hip regions, overlapping said rear portion side flaps and engaging said rear portion fastening means for said front portion engagement.

20. The method of claim 18, further comprising detaching said front portion side flap fasteners from said rear portion fasteners when a user has to use facilities to expel bodily wastes by drawing said front portion back through the crotch area between the legs of the user and up to said back waist edge and folding one said front portion side flap fastener up to same said rear portion side flap fastener that it was attached to when said article was adorned in a pant like shape, such that the genitalia is exposed and then doing the same with opposing said front portion side flap fastener to opposing said rear portion fastener.

* * * * *